US007806890B2

(12) United States Patent
McKinnon et al.

(10) Patent No.: US 7,806,890 B2
(45) Date of Patent: Oct. 5, 2010

(54) VASCULAR ACCESS DEVICE VOLUME DISPLACEMENT

(76) Inventors: Austin Jason McKinnon, 5618 Adeline Ct., Herriman, UT (US) 84065; Weston F. Harding, 2421 N. 910 West, Lehi, UT (US) 84043; Christopher N. Cindrich, 1803 E. Seven Oaks La., Draper, UT (US) 84020; Kelly D. Christensen, 1188 N. Deerfield Dr., Centerville, UT (US) 84014; S. Ray Isaacson, 4360 S. 2175 West, Roy, UT (US) 84067; Chad M. Adams, 7037 Swan Hill Dr., West Jordan, UT (US) 84084; Frank Holloway, 860 Crabappie Dr., Loveland, CO (US) 80538

( * ) Notice: Subject to any disclaimer, the term of this patent is extended or adjusted under 35 U.S.C. 154(b) by 18 days.

(21) Appl. No.: 11/829,001

(22) Filed: Jul. 26, 2007

(65) Prior Publication Data
US 2008/0027398 A1 Jan. 31, 2008

Related U.S. Application Data

(60) Provisional application No. 60/820,639, filed on Jul. 28, 2006.

(51) Int. Cl.
*A61M 39/10* (2006.01)
(52) U.S. Cl. ...................................... 604/533
(58) Field of Classification Search ............ 604/167.01, 604/264, 43, 256, 167.03, 533, 93.01, 534–536; 251/149.1
See application file for complete search history.

(56) References Cited

U.S. PATENT DOCUMENTS

| | | | |
|---|---|---|---|
| 4,765,588 A | 8/1988 | Atkinson | |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,820,601 A | 10/1998 | Mayer | |
| 5,957,898 A | 9/1999 | Jepson et al. | |
| 6,029,946 A | 2/2000 | Doyle | |

(Continued)

*Primary Examiner*—Kevin C Sirmons
*Assistant Examiner*—Michael J Anderson
(74) *Attorney, Agent, or Firm*—Mony R. Ghose; Craig Metcalf; Kirton & McConkie

(57) ABSTRACT

A medical device includes a vascular access device with an access port having a septum and a slit. The slit is formed on the inner surface of the body of the septum where the access port receives an access device that is separate from the vascular access device through the slit of the septum. A pivoting member in communication with the access port pivots when the port is accessed by an access device. The medical device may be used to control the volume displacement of a chamber within the medical device by decreasing the volume of the chamber by inserting a substance having a mass into the chamber, pivoting a structure associated with the chamber, and increasing the volume of the chamber simultaneously and commensurately with the mass of the substance inserted into the chamber.

20 Claims, 32 Drawing Sheets

U.S. PATENT DOCUMENTS

| | | |
|---|---|---|
| 6,171,287 B1 | 1/2001 | Lynn et al. |
| 6,261,282 B1 | 7/2001 | Jepson et al. |
| 6,344,033 B1 | 2/2002 | Jepson et al. |
| 6,428,520 B1 | 8/2002 | Lopez et al. |
| 6,595,964 B2 | 7/2003 | Finley et al. |
| 6,651,956 B2 | 11/2003 | Miller |
| 6,669,681 B2 | 12/2003 | Jepson et al. |
| 6,695,817 B1 | 2/2004 | Fangrow, Jr. |
| 6,840,501 B2 | 1/2005 | Doyle |
| 6,866,656 B2 | 3/2005 | Tingey et al. |
| 6,908,459 B2 | 6/2005 | Harding et al. |
| 6,916,309 B2 | 7/2005 | Fangrow, Jr. |
| 7,104,520 B2 | 9/2006 | Leinsing et al. |
| 7,184,825 B2 | 2/2007 | Leinsing et al. |
| 7,244,249 B2 | 7/2007 | Leinsing et al. |
| 2002/0193752 A1 | 12/2002 | Lynn |
| 2003/0050610 A1 | 3/2003 | Newton et al. |
| 2003/0120221 A1 | 6/2003 | Vaillancourt |
| 2004/0124388 A1 | 7/2004 | Kiehne |
| 2004/0206924 A1 | 10/2004 | Newton et al. |
| 2005/0256500 A1 | 11/2005 | Fujii |

VASCULAR ACCESS DEVICE VOLUME DISPLACEMENT

RELATED APPLICATIONS

This application claims the benefit of U.S. Provisional Application No. 60/820,639, filed Jul. 28, 2006, entitled VASCULAR ACCESS DEVICE VOLUME DISPLACEMENT, which is incorporated herein by reference.

BACKGROUND OF THE INVENTION

The present disclosure relates to the displacement of volume in medical devices such as vascular access devices to provide infusion or other therapy to patients. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by vascular access devices located outside the vascular system of a patient (extravascular devices). Extravascular devices that may access a patient's peripheral or central vasculature, either directly or indirectly, include closed access devices, such as the BD Q-SYTE™ closed Luer access device of Becton, Dickinson and Company; syringes; split access devices; catheters; and intravenous (IV) fluid chambers. A vascular access device may be indwelling for short term (days), moderate term (weeks), or long term (months to years). A vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other extravascular device attached thereto, may have a single lumen or multiple lumens for infusion of many fluids simultaneously.

The proximal end of a vascular access device commonly includes a Luer adapter to which other medical devices may be attached. For example, an administration set may be attached to a vascular access device at one end and an IV bag at the other. The administration set is a fluid conduit for the continuous infusion of fluids and pharmaceuticals. Commonly, an TV access device is a vascular access device that may be attached to another vascular access device, closes or seals the vascular access device, and allows for intermittent infusion or injection of fluids and pharmaceuticals. An IV access device may comprise a housing and a septum for closing the system. The septum may be opened with a blunt cannula or a male Luer of a medical device.

Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Vascular access device infection resulting in CRBSIs may be caused by pathogens entering the fluid flow path from refluxed or displaced blood subsequent to catheter insertion. Studies have shown the risk of CRBSI increases with catheter indwelling periods. This may be due, at least in part, to the reflux or displacement of blood from the vascular system of a patient to an extravascular device, such as the catheter. When contaminated, pathogens adhere to the vascular access device, colonize, and form a biofilm. The biofilm is resistant to most biocidal agents and provides a replenishing source for pathogens to enter a patient's bloodstream and cause a BSI.

Certain extravascular devices can operate with each other to form a continuous, extravascular system that provides fluid access to the vascular system, yet is entirely sealed from the external surrounding environment. Such a sealed system limits or supposedly prevents unwanted bacteria from entering from the external surrounding environment through the extravascular devices to the vascular system of a patient.

However, a sealed system of extravascular devices (extravascular system) may function as a closed or sealed vacuum, capable of drawing blood, and consequently a culture for infection, into the extravascular system. As devices are twisted off or otherwise removed from the extravascular system, the volume of the extravascular system is sometimes slightly increased. Because extravascular systems are often less elastic than a patient's vascular system, when the volume of the extravascular system is increased, the volume of a patient's vascular system is decreased under a vacuum pressure from the extravascular system. When the volume of the vascular system decreases, blood flows or is sucked from the vascular system to the extravascular system. Further, as pressure in the extravascular system decreases below the vascular pressure of a patient, either as a result of a change in volume in the extravascular system or another event, blood will flow from the vascular system to the extravascular system.

As recognized in conjunction with the present invention, even a temporary presence of blood within an extravascular system can cause future operational challenges for that extravascular system. For example, blood that clots in the end of a catheter of an extravascular system can block future fluid flow between the extravascular system and a vascular system. If drugs and other fluid substances are forced through the extravascular system causing the blood clot to dislodge from the extravascular system, the blood clot will enter the vascular system causing a dangerous embolism within the patient. Finally, as discussed above, even the rapid entry and exit of blood into the catheter tip of an extravascular system will leave a residue of protein, bacteria, and other pathogens on the inner wall of the catheter. This residue may become a breeding ground for bacteria to grow, and after a given period of time, will cause the formation of a harmful biofilm that is difficult to remove or bypass during extravascular system operation.

Therefore, a need exists for systems and methods that avoid or limit the reflux or displacement of blood from a patient's vascular system into an extravascular system that is connected to the patient's vascular system.

BRIEF SUMMARY OF THE INVENTION

The present invention has been developed in response to problems and needs in the art that have not yet been fully resolved by currently available extravascular systems, devices, and methods. Thus, these developed systems, devices, and methods provide an extravascular system that may be connected to a patient's vascular system and will limit or prevent the flow, reflux, or displacement of blood from the vascular system to the extravascular system.

A medical device may include a vascular access device with an access port having a septum and a slit. The slit is formed on the inner surface of the body of the septum. The access port may receive an access device that is separate from the vascular access device through the slit of the septum. A pivoting member in communication with the access port pivots when the port is accessed by an access device.

The pivoting member may be one of the following types of devices: a T-bone shaped rigid structure, a T-bone shaped rigid structure on the outer surface of the septum, an L-shaped rigid structure, a gate held under the tension of a torsion spring, a rib, a wedge, a split wedge, a four-bar mechanism, a semi-rigid or rigid buckling member, a rigid member displaced by a disturbed air pressure chamber, a rigid member displaced by a disturbed pressure sensitive chemical, and/or a spring finger. The pivoting member may articulate upon a bistable spring, a torsion spring, or other spring or tension creating member. The pivoting member may form a curved or other structure.

A method of employing the medical device may be used to control the volume displacement within a chamber of the medical device. The method may include decreasing the volume of a chamber of an extravascular system by inserting a substance having a mass into the chamber, pivoting a structure within the extravascular system, and increasing the volume of the chamber simultaneously and commensurately with the mass of the substance inserted into the chamber. The substance may be either a fluid or a mechanical structure of a medical device, such as the tip of a syringe.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
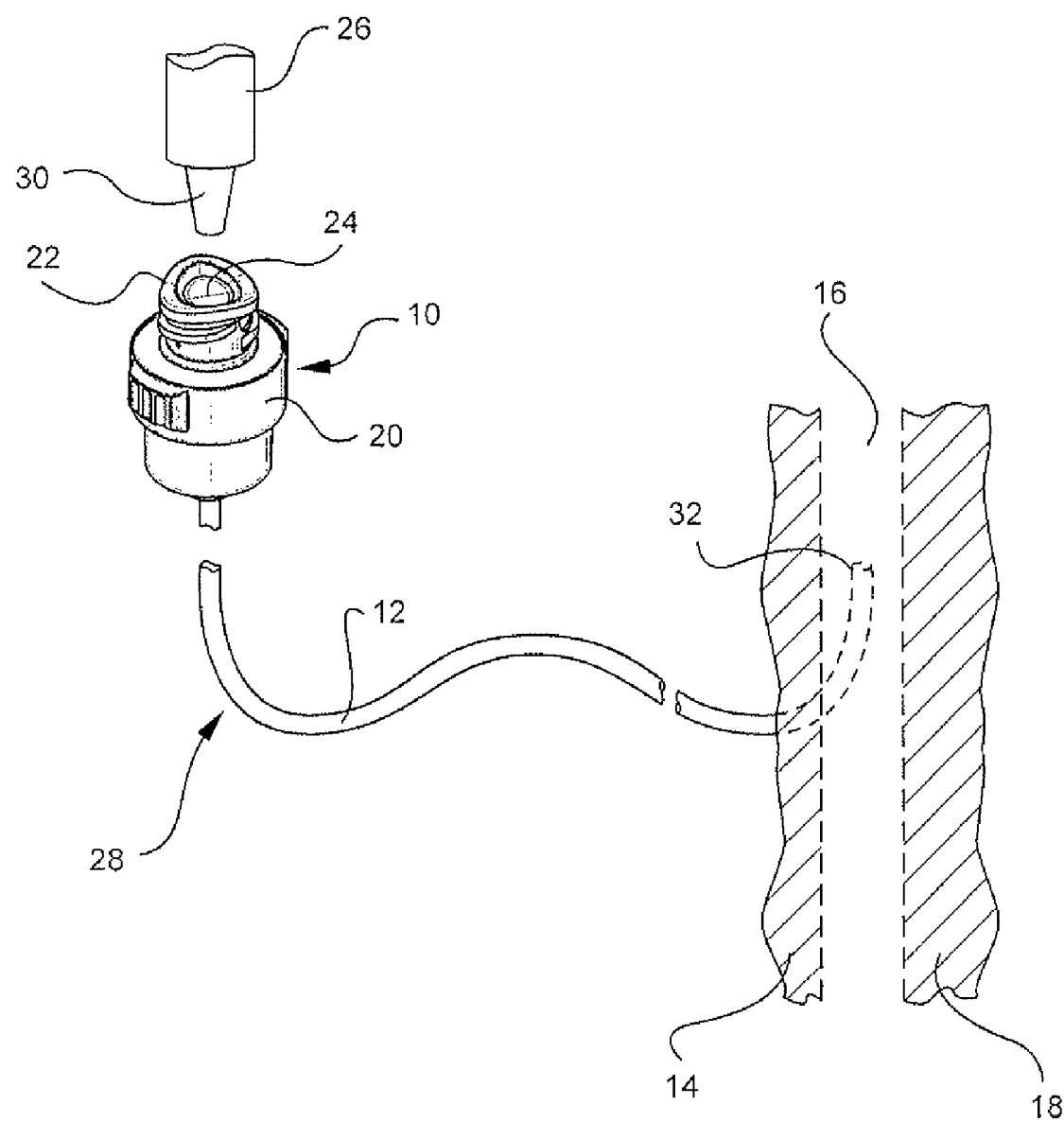
FIG. 1 is a perspective view of an extravascular system connected to the vascular system of a patient.

Referring now to FIG. 1, a vascular access device (also referred to as an extravascular device, intravenous access device, and/or access port) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 also includes a member (discussed with reference to the figures below) capable of creating a volume within the vascular access device 10 and/or the extravascular system 28 to which the vascular access device 10 is connected. The member capable of creating this volume creates the volume when a tip 30 of the separate device 26 is inserted into the vascular access device 10 through the slit 24 of the septum 22. Normally, when the tip 30 is inserted into the device 10, the volume of the extravascular system 28 is decreased, causing fluid to flow from the system 28 into the blood vessel 16. Conversely, under normal conditions, when the tip 30 is removed from the device 10, the volume of the extravascular system 28 is increased, causing blood to flow from the blood vessel 16 into the system 28 by entering through the end 32 of the catheter 12.

As mentioned throughout this description, even a temporary presence of blood within an extravascular system 28 can cause future operational challenges for that extravascular system 28. These problems may include blood clots, fluid flow barriers, embolisms, and the production of harmful biofilm. Thus, the devices disclosed herein are provided to avoid reflux or drawback of blood from the blood vessel 16 into the catheter 12. The devices may include a member capable of creating a volume when the separate device 26 is inserted into the vascular access device 10 and will permit the created volume to decrease to its original size. When the volume decreases to its original size, the decrease in volume will offset any volume displaced such that upon removal of the separate access device 26. The volume offset will either result in no net displacement of fluid between the system 28 and the vessel 16 or will result in fluid being forced distally from the vascular access device 10 or other medical device toward the vascular system of a patient. This further avoids creation of a vacuum or a pressure differential between the system 28 and the vessel 16 that would cause blood to flow or be sucked from the blood vessel 16 into the catheter 12.

Figure 2:
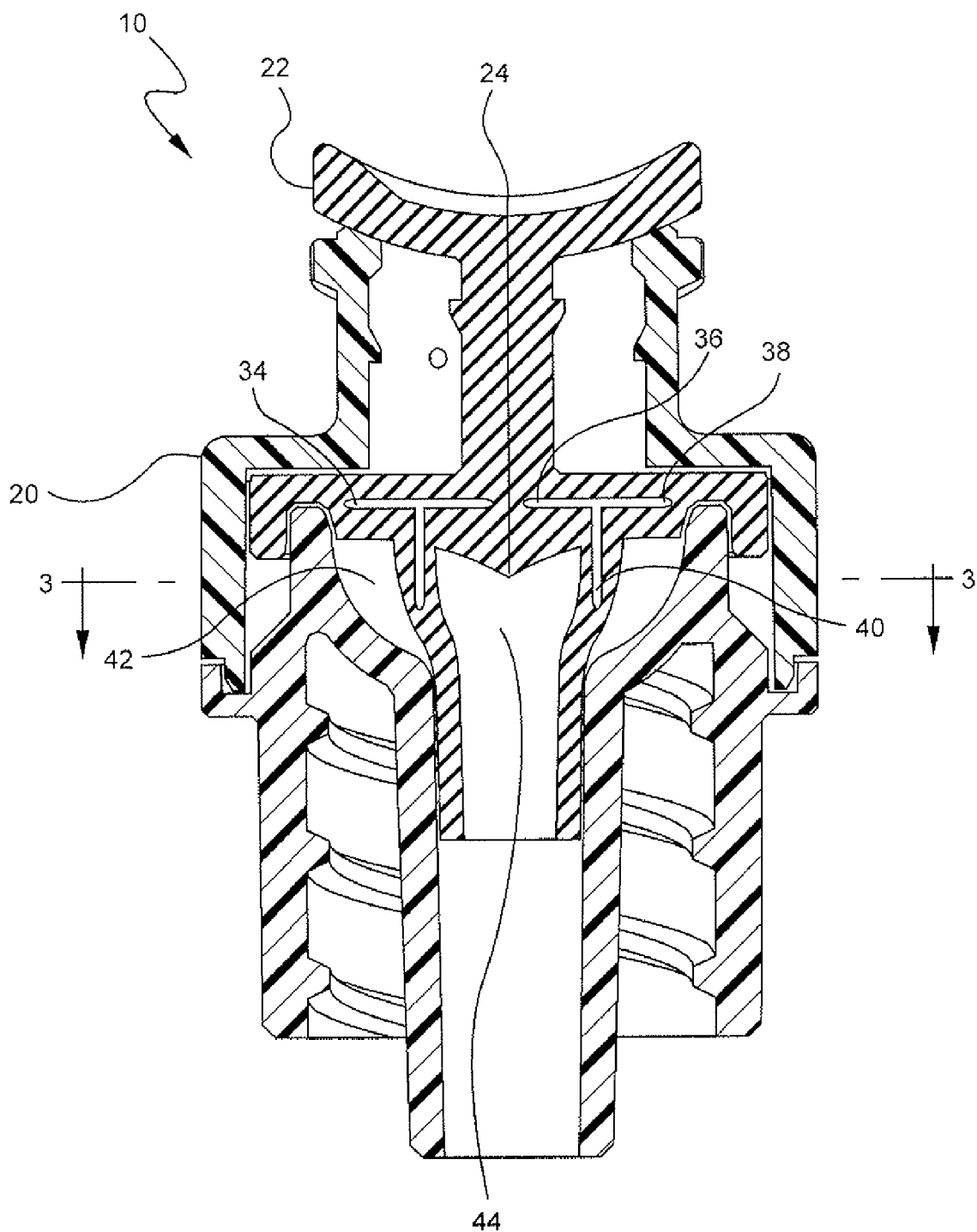
FIG. 2 is a cross section view of a vascular access device with pivoting T-bone members.

Referring now to FIG. 2, a vascular access device 10 includes at least one rigid, pivoting member 34 within the wall of the septum 22. The pivoting member 34 is rigid in relation to the materials of its surrounding environment. In this embodiment, the septum 22 is formed of silastic or other pliable, elastic material. Thus, the pivoting member 34 may be formed of hardened rubber, plastic, metal, alloy, or other relatively rigid material. The pivoting member 34 is shaped as a T-bone structure with a first end 36 of the top of the "T" extending towards the slit 24 of the septum. A second end 38 of the top of the "T" extends towards the edge of the body 20 of the vascular access device 10. The base 40 of the "T" extends into a separation of an outer chamber 42 and an interior chamber 44 of the device 10.

Figure 3:
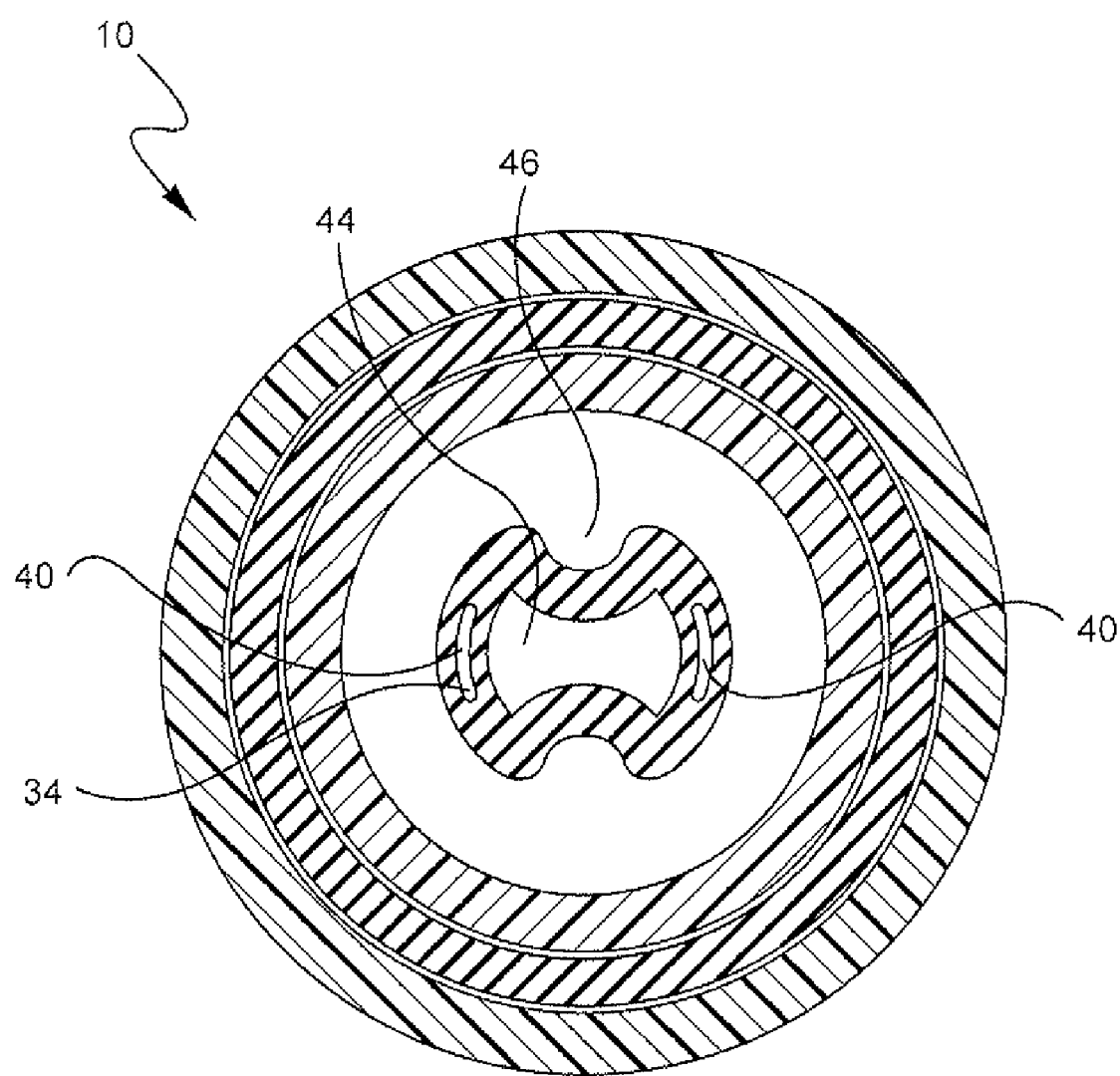
FIG. 3 is a cross section view of the vascular access device of FIG. 2 taken along lines 3-3

FIG. 3 is a cross-section view of the vascular access device 10 of FIG. 2 taken along lines 3-3. Device 10 includes the base 40 of the "T" of the pivoting member 34 embedded within a silastic material. This silastic material is an extension of the septum 22 and has been manufactured, extruded, molded, heat-treated, or otherwise formed to include at least one fold 46 along its cross section. The fold 46 remains until a separate device 26 is placed within the slit 24 of the septum 22 causing the rigid member 34 to open. When the rigid member 34 opens, the base members 40 move from a first resting position shown in FIG. 3 to a second opened position to be shown in FIG. 5. When the base members 40 are moved from a first resting position to a second opened position, the at least one fold 46 straightens causing the volume of the outer chamber 42 to decrease and the volume of the interior chamber 44 to increase.

Figure 4:
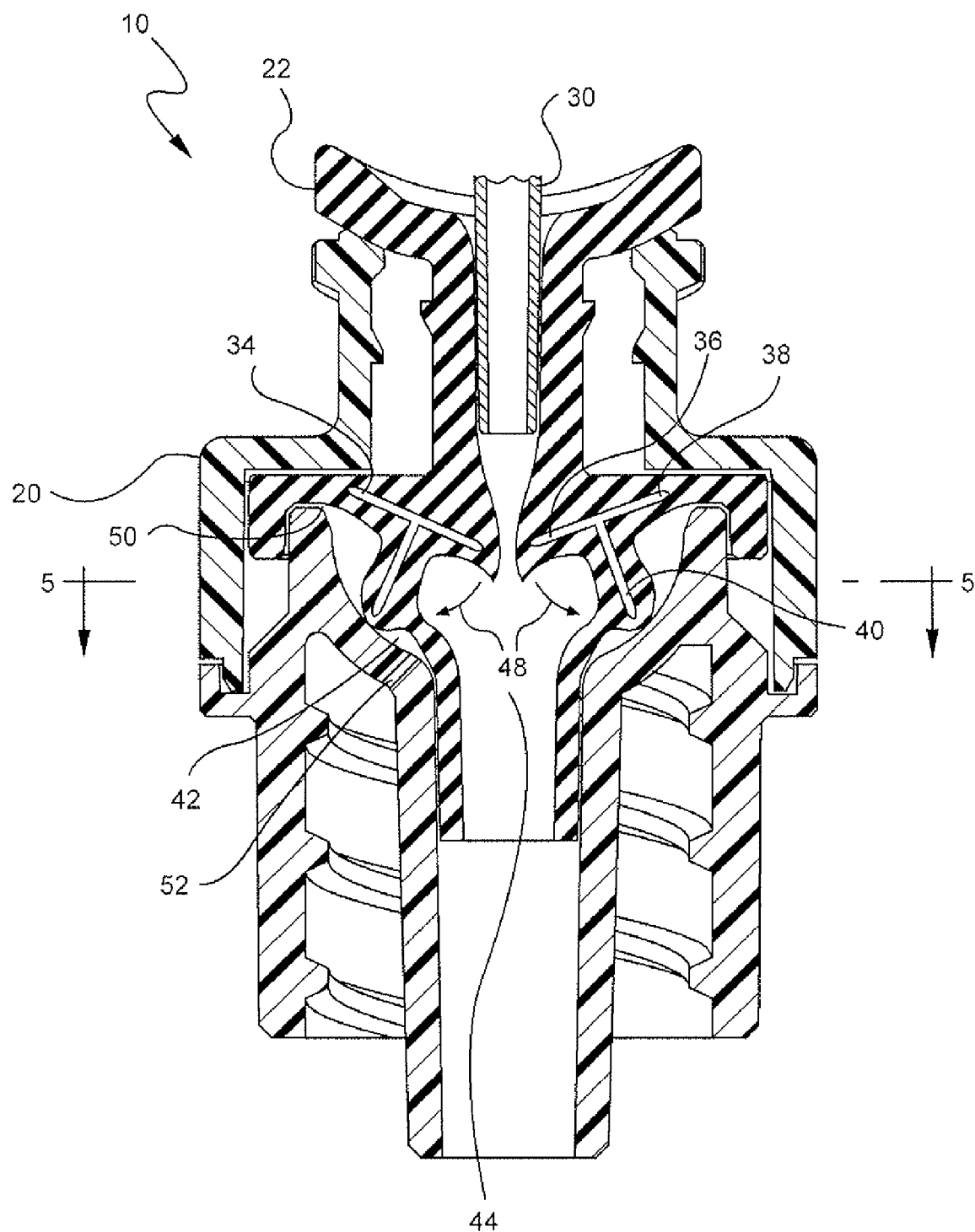
FIG. 4 is a cross section view of the vascular access device of FIG. 2 shown with the tip of a separate device inserted.

Referring now to FIG. 4, a vascular access device 10 of FIG. 2 is shown with the tip 30 of the separate device 26 inserted within the septum 22. As the tip 30 is inserted into the septum, the walls of the septum begin to move downward and outward in a direction 48. As the walls of the septum 22 are moved in a direction 48 under the influence of the tip 30, rigid members 34 pivot outward causing the first ends 36 to move downward and the base members 40 to move outward towards the body 20 of the vascular access device 10.

The first ends 36 move downward, away from the direction of the advancing tip 30 as the second ends 38 pivot against a fulcrum 50 placed within the body 20 of the vascular access device 10. As the base members 40 are moved outwards towards the body 20 of the device 10, the volume of the outer chamber 42 decreases while the volume of the interior chamber 44 increases. At least one channel 52 may need to be placed within the body 20 of the vascular access device 10 in order to permit the air within the outer chamber 42 to escape the outer chamber 42 when the base members 40 are moved into the space of the outer chamber 42. The at least one channel 52 will permit the volume of the outer chamber 42 to decrease without any pressure buildup that would require an increase in insertion force during tip 30 insertion.

Figure 5:
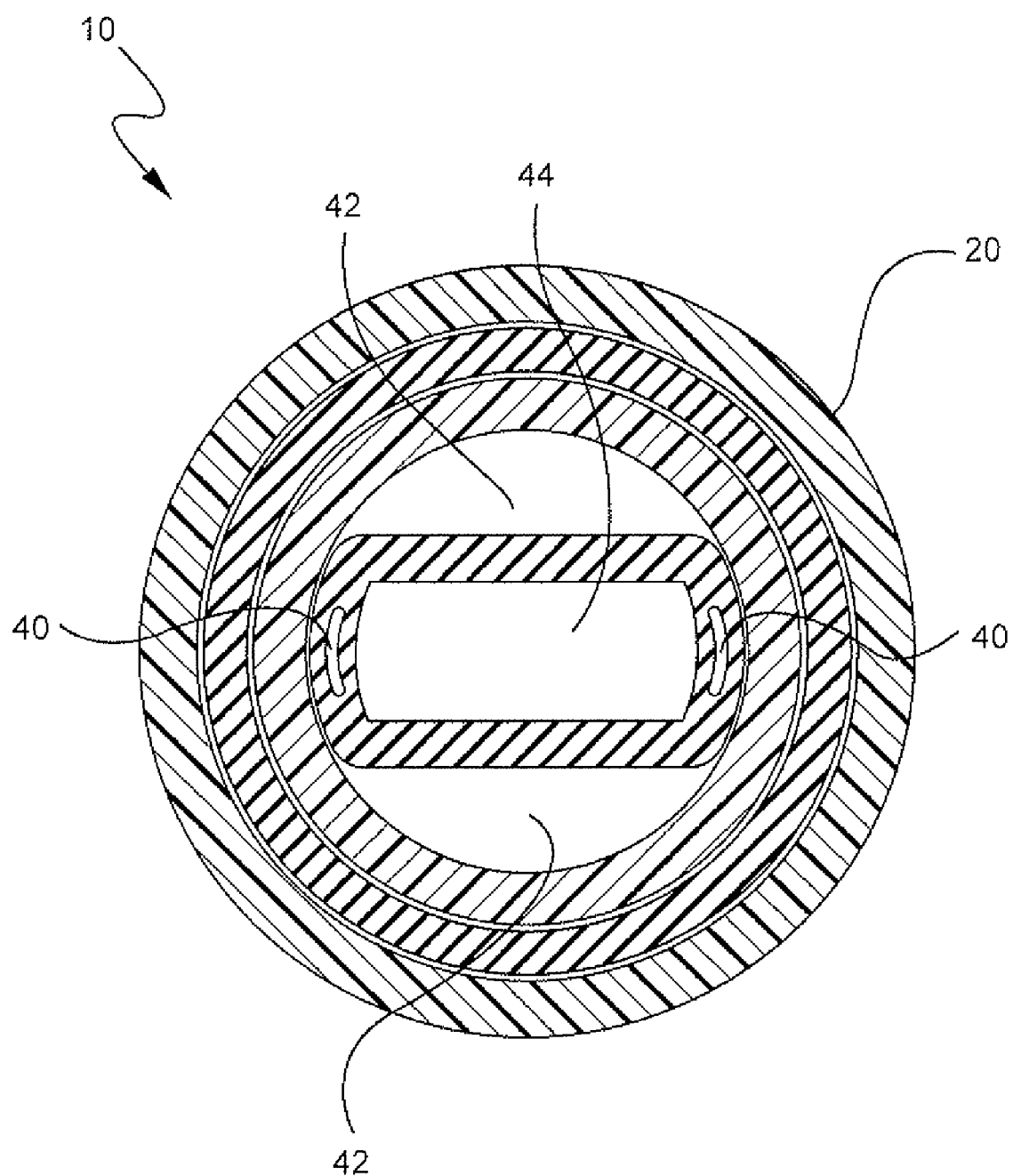
FIG. 5 is a cross section view of the vascular access device of FIG. 4 taken along lines 5-5.

FIG. 5 is a cross-section taken along lines 5-5 of FIG. 4. The vascular access device 10 includes the base member 40 extended towards the body 20 of the vascular access device 10. With the base members 40 extended, the silastic material no longer includes at least one fold 46. Rather the folds 46, as show in FIG. 3, have been extended to form a straight section of the silastic member such that the volume of the outer chamber 42 has been decreased and the volume of the interior chamber 44 has been increased.

When the tip 30 of a separate device 26 is removed from the slit 24 of the septum 22, the rigid member 34 closes under the force of the formed silastic material that is an extension of the septum 22. As mentioned earlier with reference to FIG. 3, the silastic material has been manufactured or otherwise formed to include at least one fold (FIG. 3) along its cross-section. These folds 46 exist when the silastic material is in its resting position. Thus, when the silastic material is stretched as shown in FIG. 5, once the tip 30 of the separate device 26 is removed, the natural force of the formed silastic material will cause the silastic material to return to its original position as shown in FIG. 3. When the formed silastic material returns to its original position, the base members 40 will likewise return to its original position causing the volume of the outer chamber 42 to increase while the volume of the interior chamber 44 decreases. This decrease of volume within the interior chamber 44 will result in either no net volume displacement within the interior chamber 44 or will result in a volume that is displaced from the interior chamber 44 downstream through the extravascular system 28 and into the vascular system of a patient.

Figure 6:
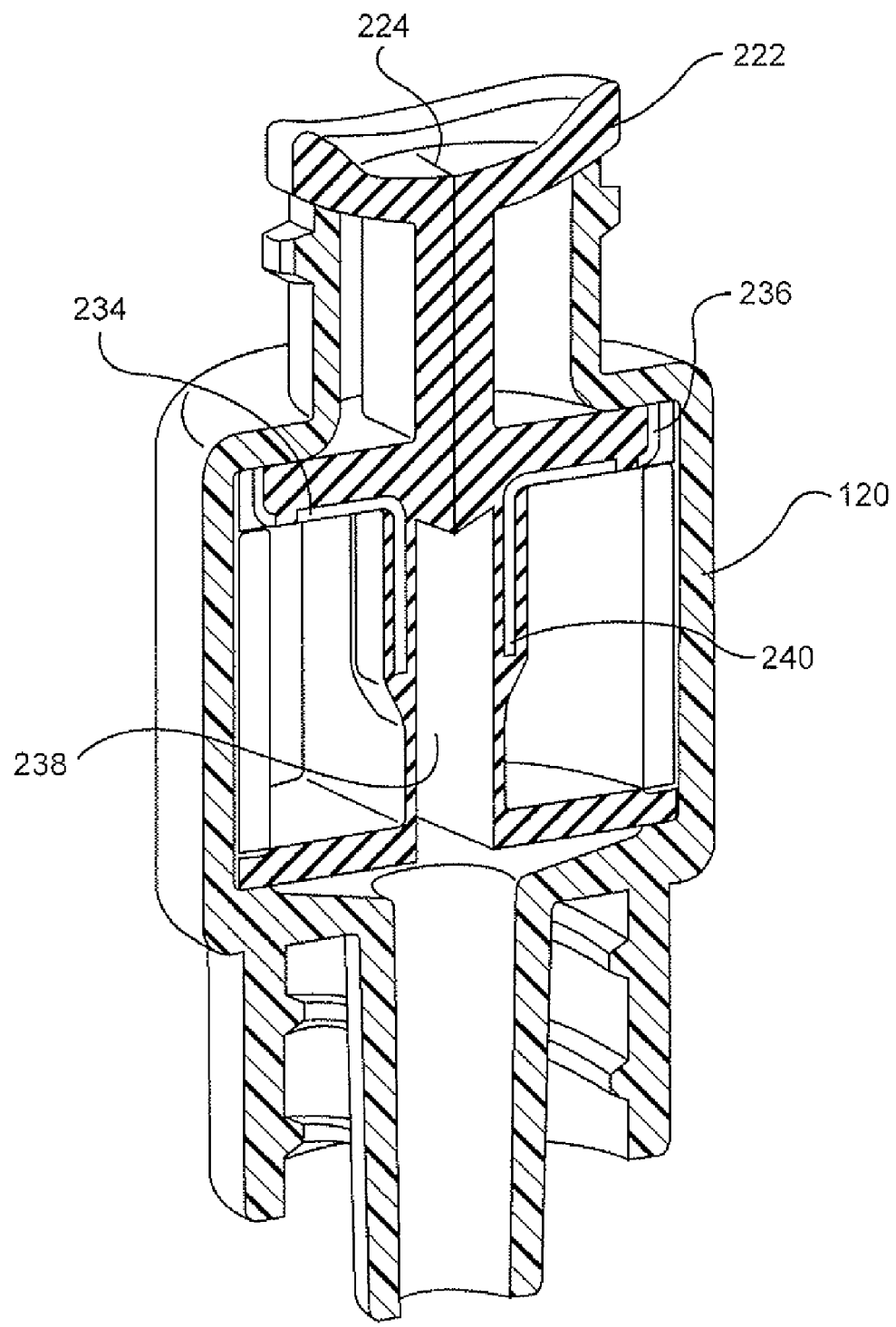
FIG. 6 is a cross section view of a vascular access device having an alternative embodiment of a pivoting member.

Referring now to FIG. 6, a vascular access device 210 includes at least one rigid, pivoting member 234 within the wall of the septum 222. The pivoting member 234 is rigid in relation to the materials of its surrounding environment. As with embodiments previously discussed, the septum 222 is formed of silastic or other pliable, elastic material. Thus, pivoting member 234 may be formed of hardened rubber, plastic, metal, alloy, or other relatively rigid material. The L-shaped member may be encased in the silastic as illustrated in FIG. 6, or may be bonded or attached to the silastic by means well known to those of skill in the art.

In this embodiment, the pivoting member 234 is shaped as an L-shaped structure with a first end 236 of the top of the "L" extending towards the slit 224 of the septum. The base 240 of the "L" extends downwardly along the channel through the septum 210. Thus, when a separate extravascular device 26 is inserted into the septum, the rigid L-shaped pivoting member 234 causes the channel 238 through the septum to increase in volume. When the extravascular device 26 is removed and the channel 238 returns to its original configuration, the volume within the channel 238 is reduce, thus preventing blood or other fluid from being drawn up into the extravascular system 28.

Figure 7:
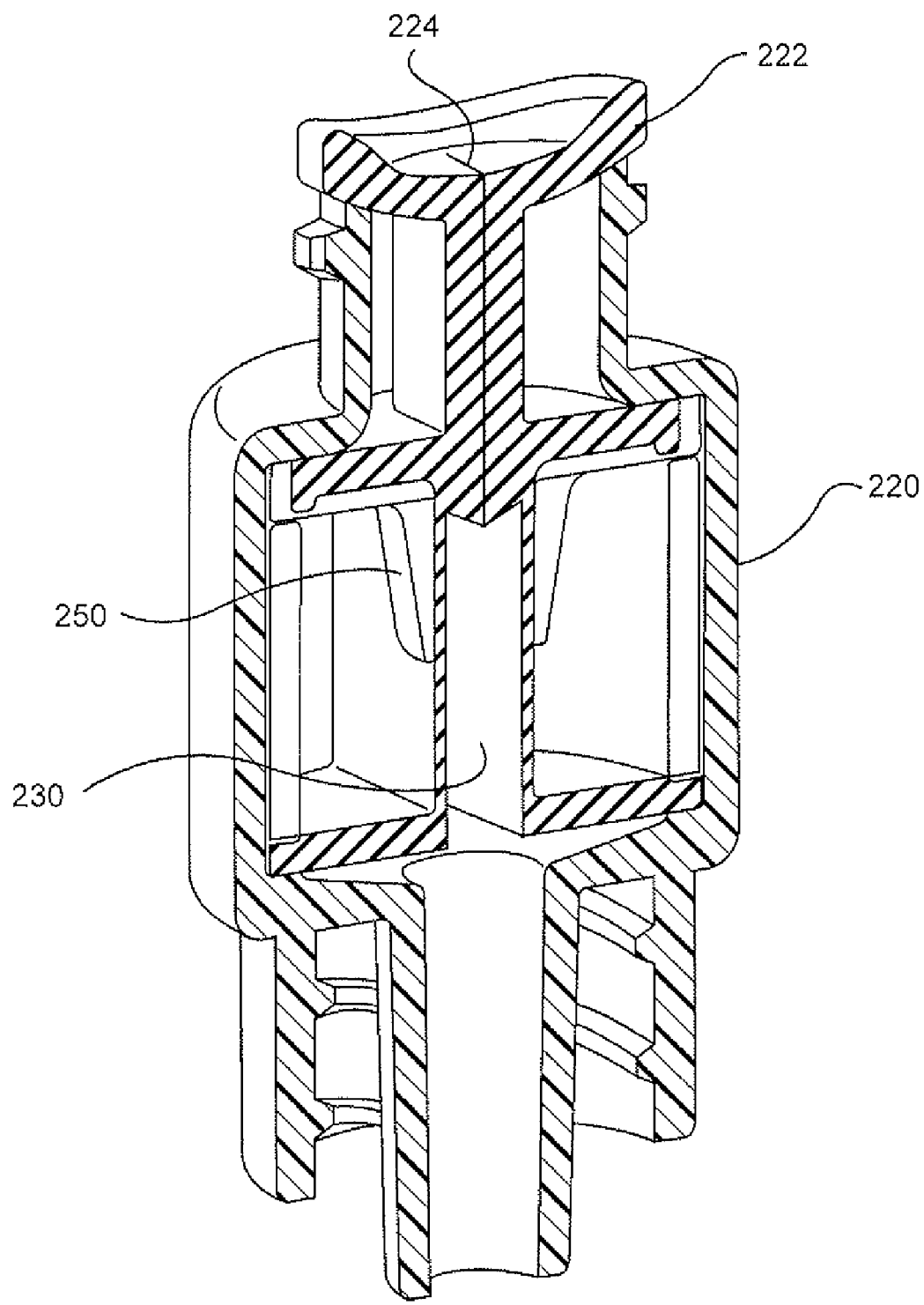
FIG. 7 is a cross section view of a vascular access device having a further embodiment of a pivoting member.

FIG. 7 illustrates an alternative embodiment of the device in which the L-shape pivoting member 234 is replaced by a rigid wedge member 250. Wedge member 250 can be made of rigid plastic or other similar materials. Once again, wedge member 250 provides sufficient rigidity to cause the channel 230 to expand in volume as a separate extravascular device 26 is inserted into the device 210. Thus, when the extravascular device 26 is removed, the volume decreases to its original state, preventing blood or other fluids from being drawn into the extravascular system 28.

Figure 8:
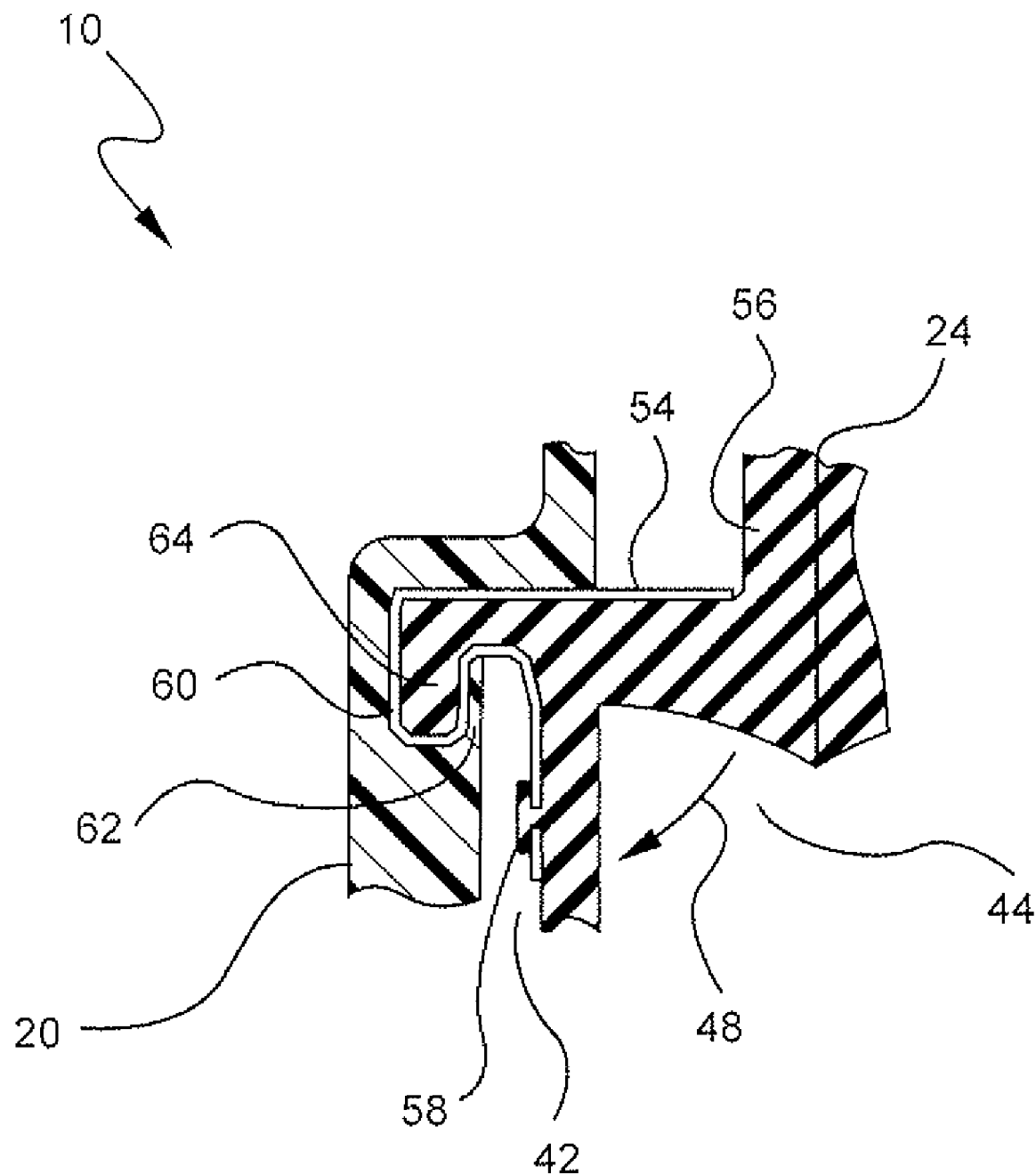
FIG. 8 is a partial cross section view of a vascular access device with an external pivoting member.

Referring now to FIG. 8, a partial cross-section view of a vascular access device 10 shows a rigid, folding member 54 located on the external surface of a silastic septum 56. The silastic septum 56 includes a knob 58 on its exterior surface to which the pivoting member 54 is attached. The pivoting member 54 also includes an elbow 60 housed within a fulcrum 62 of the body 20 of the vascular access device 10. The elbow 60 houses a flap 64 that extends from the body 20 of the septum 56. In use, when a separate device 26 is placed within the slit 24 of the septum 56, the body 20 of the septum 56 is biased downward and outward in a direction 48, causing the knob 58 and/or any portion of the entire structure of the pivoting member 54 to bias downward and outward in the direction 48. As the pivoting member 54 pivots in the direction 48, the volume of the interior chamber 44 is increased while the volume of the outer chamber is decreased.

Figure 9:
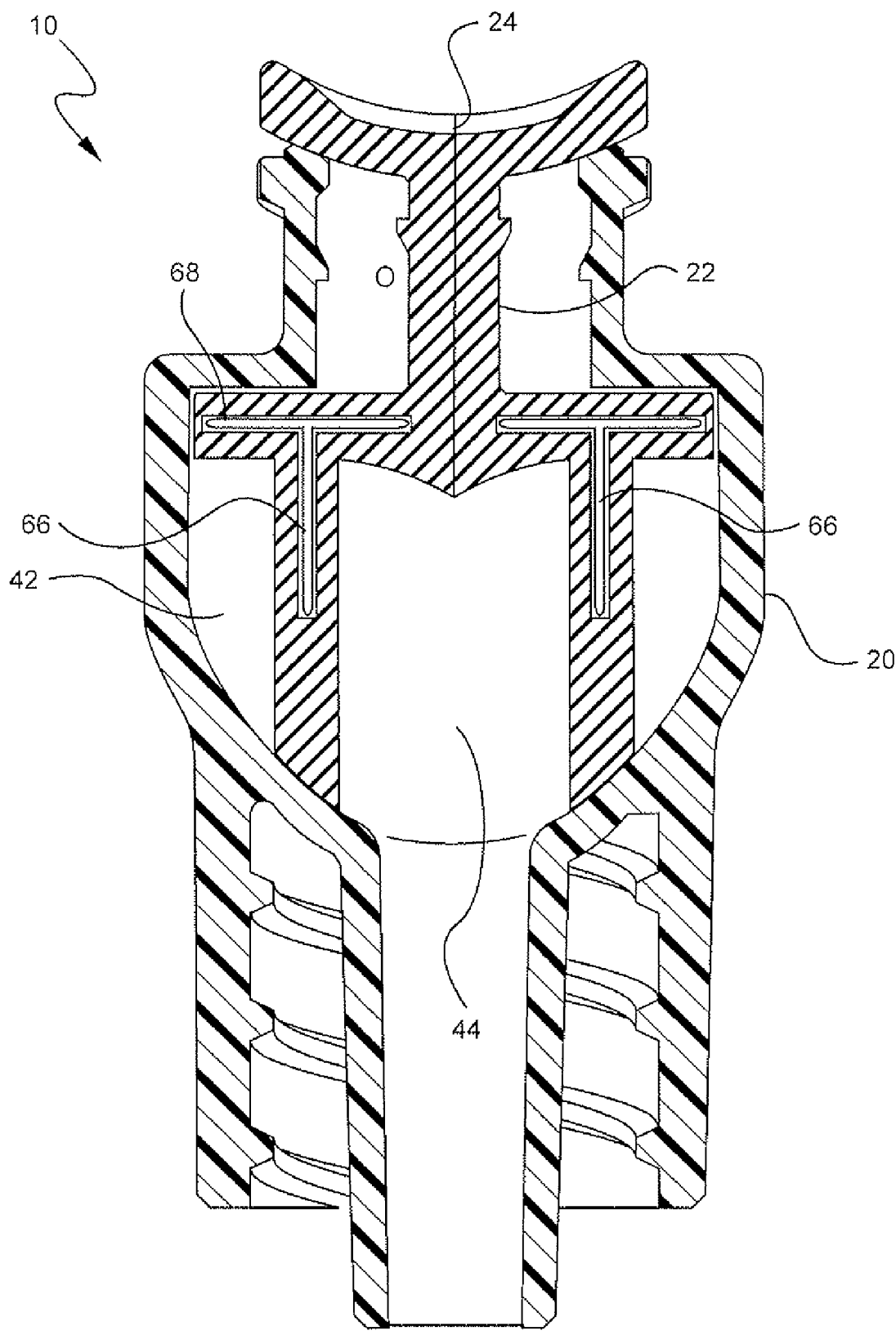
FIG. 9 is a cross section view of a vascular access device with a bistable spring pivoting member

Referring now to FIG. 9, a vascular access device 10 includes a rigid, pivoting member 66 embedded within the material of a silastic septum 22. The pivoting member 66 includes a bistable spring 68 along the top of the "T" of the pivoting member 66.

Figure 10:
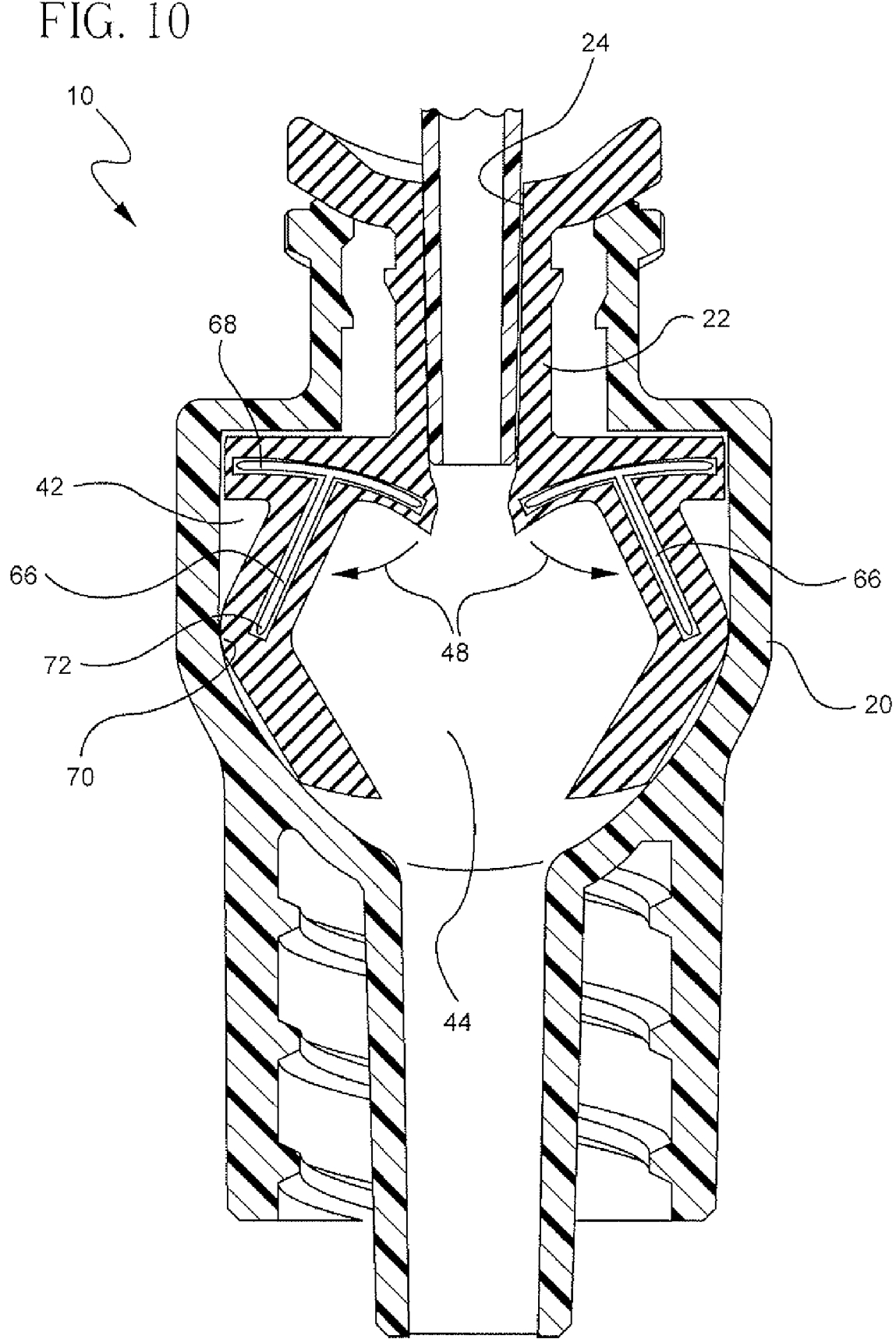
FIG. 10 is a partial cross section view of the vascular access device of FIG. 9 with the bistable spring pivoting member actuated in an open position.

FIG. 10 is a partial cross section view of the device 10 of FIG. 9. As illustrated in FIG. 10, the bistable spring 68 of the pivoting member 66 is a beam that snaps open after a predetermined amount of pressure has been applied to the bistable spring 68. In use, as the tip 30 of a separate device 26 is advanced through the slit 24 of the septum 22, the septum 22 begins to open in an outward direction causing pressure to build upon the bistable spring 68. After a given amount of pressure has been placed on the bistable spring 68, the beam of the bistable spring 68 will snap open causing the pivoting member 66 to pivot upon a fulcrum 70 of the body 20, which in turn causes the base 72 of the pivoting member 66 to move downward and outward in a direction 48. When the base member 72 of the pivoting member 66 moves toward the body 20, the volume of the interior chamber 44 is increased and the volume of the outer chamber 42 is decreased.

A bistable spring may be used with any of the above illustrated embodiments or with any of a number of the following embodiments described throughout this detailed description. The properties of the bistable spring may preferably be employed when a rapid increase in volume within an interior chamber is desired when a separate device 26 is introduced into the vascular access device 10. Similarly, the properties of the bistable spring may also preferably be employed when a rapid decrease in volume of an interior chamber is desired upon retraction and/or removal of a separate device 26 from the vascular access device 10.

In some embodiments, a gradual increase in volume of an interior chamber may be desired as a separate device is gradually inserted into the slit of the septum of the device. In these embodiments, as the separate device is gradually inserted, the opening of the septum decreases the volume of the interior chamber, while the opening of a rigid member simultaneously increases the volume of the interior chamber, offsetting the decrease of volume caused by the insertion of the separate device. In this manner, during the initial entry of the separate device into the septum, all the way through full engagement and full removal of the separate device from the septum, there will be no net change in volume of the interior chamber. Thus, with no net change in volume of the interior chamber during use of the vascular access device, any potential displacement of fluid into and out of a patient's vascular system is avoided.

Figure 11:
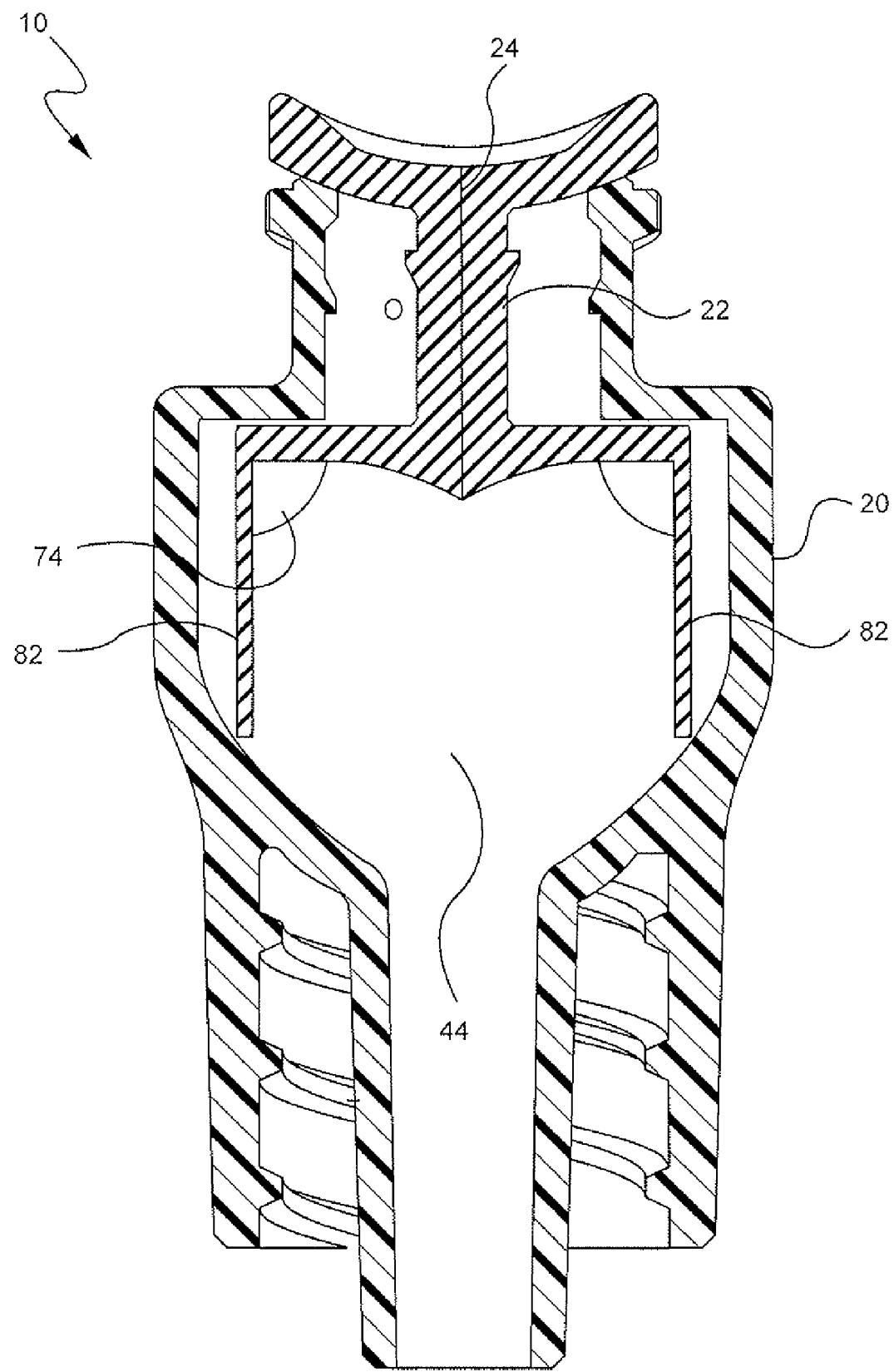
FIG. 11 is a partial cross section view of a vascular access device with a rigid pivoting member.

Referring now to FIG. 11, a vascular access device 10 includes at least one rigid member 74 in the shape of a wedge placed below the slit 24 of a septum 22 when the device 10 is in a resting state.

Figure 12:
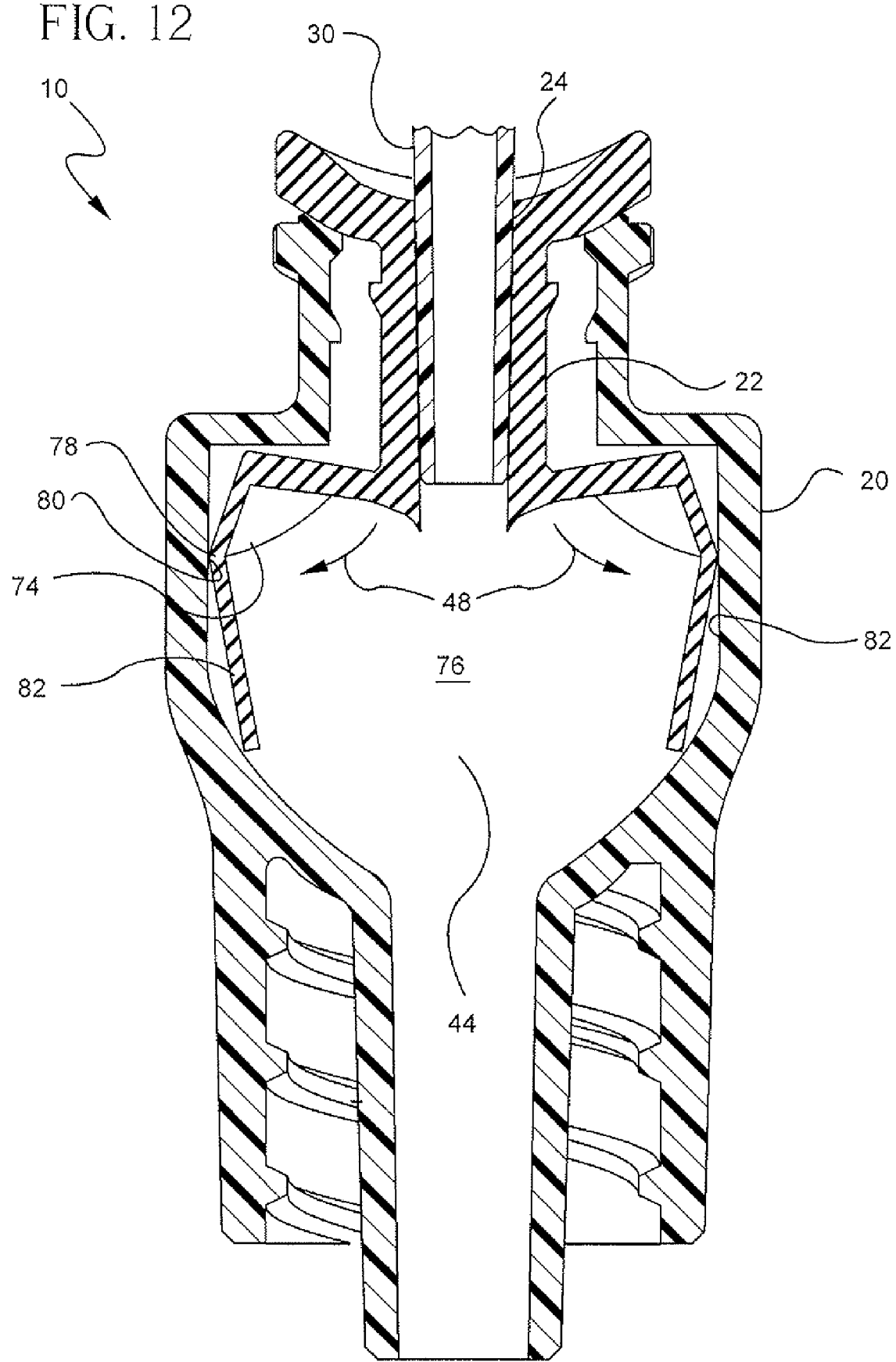
FIG. 12 is a partial cross section view of the vascular access device of FIG. 11 with the tip of a separate device inserted.

Referring now to FIG. 12, when the tip 30 of a separate device 26 is inserted into the septum 22, the rigid members 74 are biased downward and outward in a direction 48 causing an increase in volume within an interior chamber 44. The increased volume of interior chamber 44 is illustrated as volume 76. The rigid members 74 may be embedded, or surrounded, by an elastic material, such as silastic. The silastic may be attached at an elbow 78 of the silastic to a fulcrum 80 of the body 20 of the vascular access device 10. A lower portion 82 of the elastic material will stretch to enable the rigid member 74 to create the additional volume 76 when the tip 30 is inserted into the septum 22.

Figure 13:
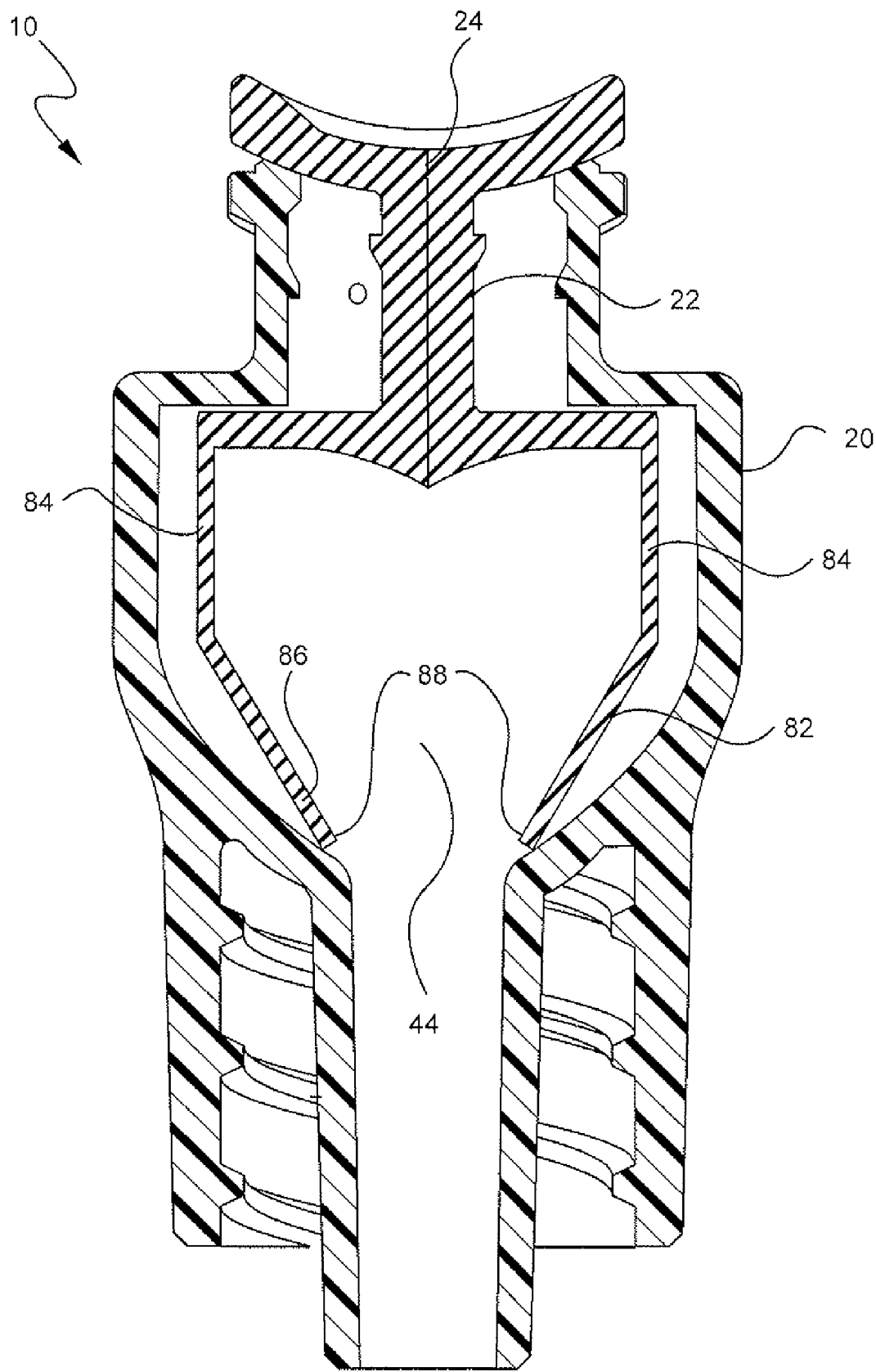
FIG. 13 is a partial cross section view of a vascular access device with a rigid pivoting member.

Referring now to FIG. 13, a vascular access device 10 includes a rigid member 84 such as a rigid rib having a structure that is continuous with a silastic or other elastic septum 22 and an elastomer 86. The elastomer 86 is attached to the base of the rib 84 while the septum 22 is attached to the head of the rib 84. The rib or rigid member 84 may also be embedded or otherwise attached to a continuous elastomer as illustrated throughout the embodiments of this detailed description. As mentioned earlier, one end of the elastomer 86 is attached to the rib 84, while the other end of the elastomer is fixed at a point 88 within the vascular access device 10. Because the elastomer 86 is fixed at a point 88 and attached to the base of the rib 84, when the rib 84 pivots, causing the elastomer 86 to stretch, the elastomer 86 will not be dislodged from its fixed point 88.

Figure 14:
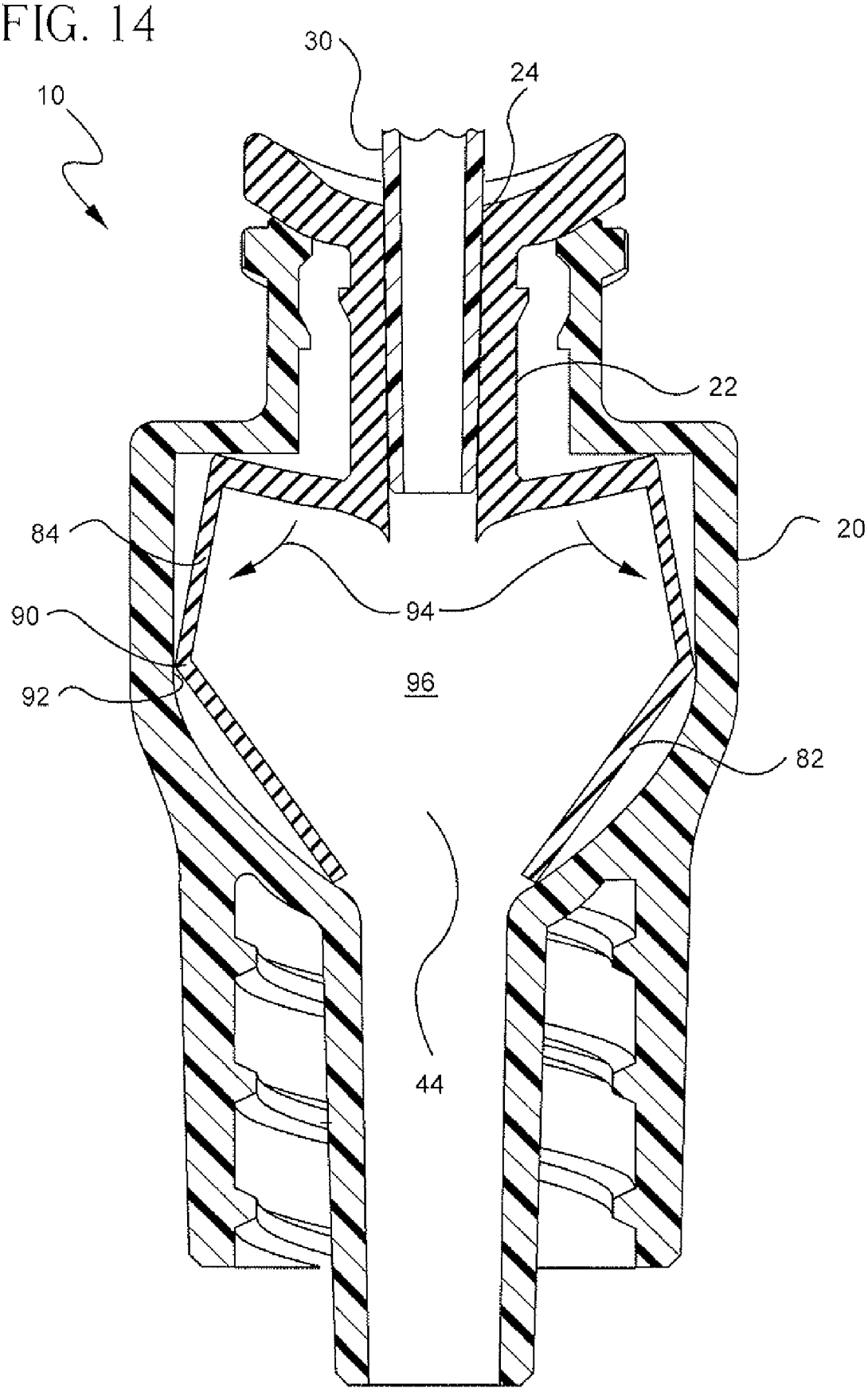
FIG. 14 is a partial cross section view of the vascular access device of FIG. 13 with the tip of a separate device inserted.

Referring now to FIG. 14, the vascular access device 10 of FIG. 13 shows the tip 30 of an external device 26 inserted within the septum 22. As the tip 30 advances through the septum 22, the rigid members 84 pivot upon an elbow 90 that communicates with a fulcrum 92 of the body 20 of the vascular access device 10. When the rigid members 84 pivot, the base of the rigid members 84 moves in an outward direction 94 stretching the elastomer 86 and creating an increased amount of volume 96 within the interior chamber 44. When the tip 30 of the external device 26 is removed from the septum 22, the pivoting members 84 return to their original resting position as shown in FIG. 13, causing the elastomers 86 to return to their original position and the volume gained 96 to be decreased to an original volume of the interior chamber 44. A similar decrease in volume occurs with reference to FIGS. 11 and 12 when the tip 30 is removed from the device 10 of that particular embodiment.

Figure 15:
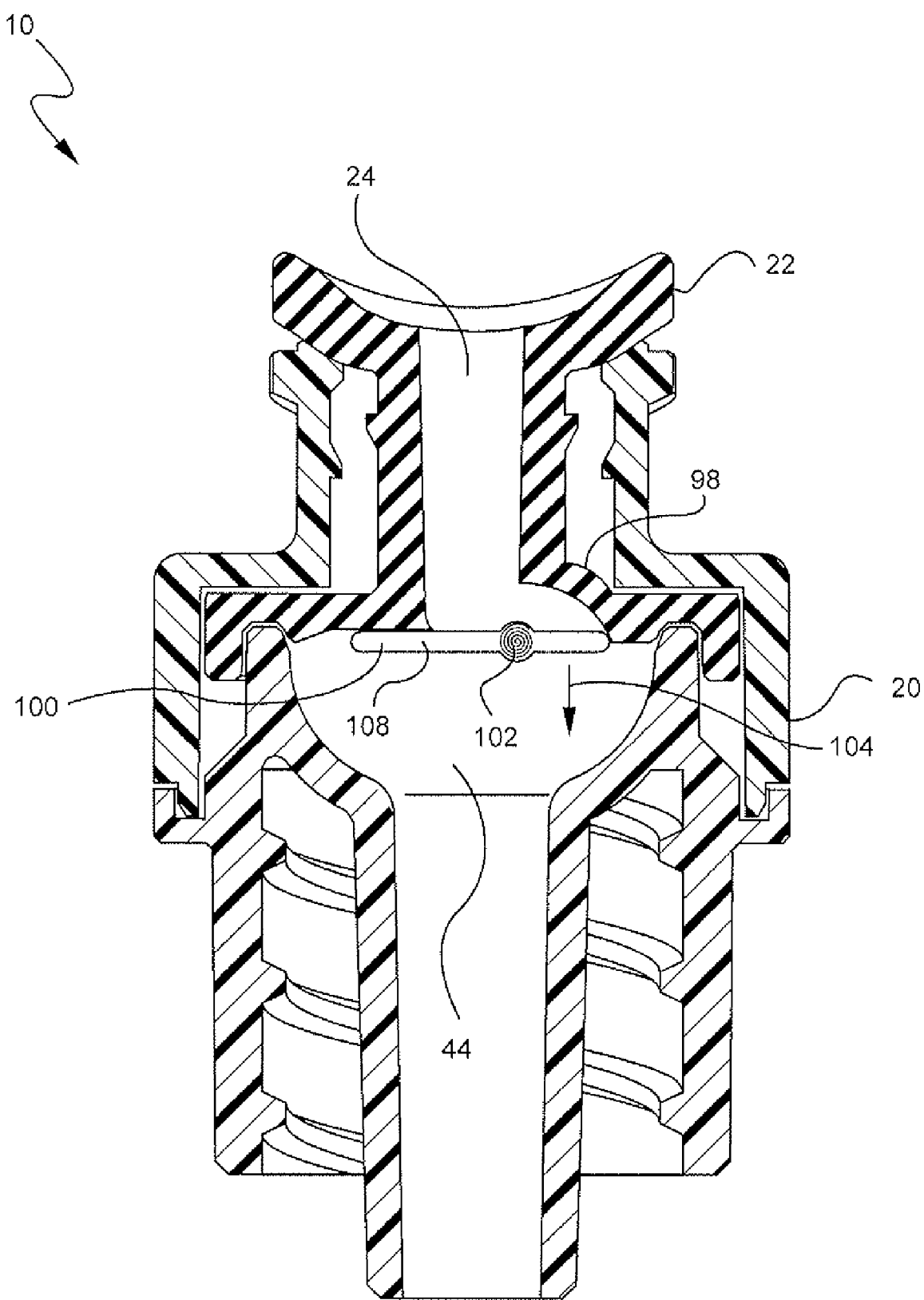
FIG. 15 is a partial cross section view of a vascular access device and closed spring loaded valve.

Referring now to FIG. 15, a vascular access device 10 includes a septum 98 that is sealed by a rigid, pivoting member 100 which pivots on a torsion type spring 102. The tension of the spring 102 biases the pivoting member 100 in a clockwise direction 104. In its resting state, the pivoting member 100 seals the septum 98 in a closed position.

Figure 16:
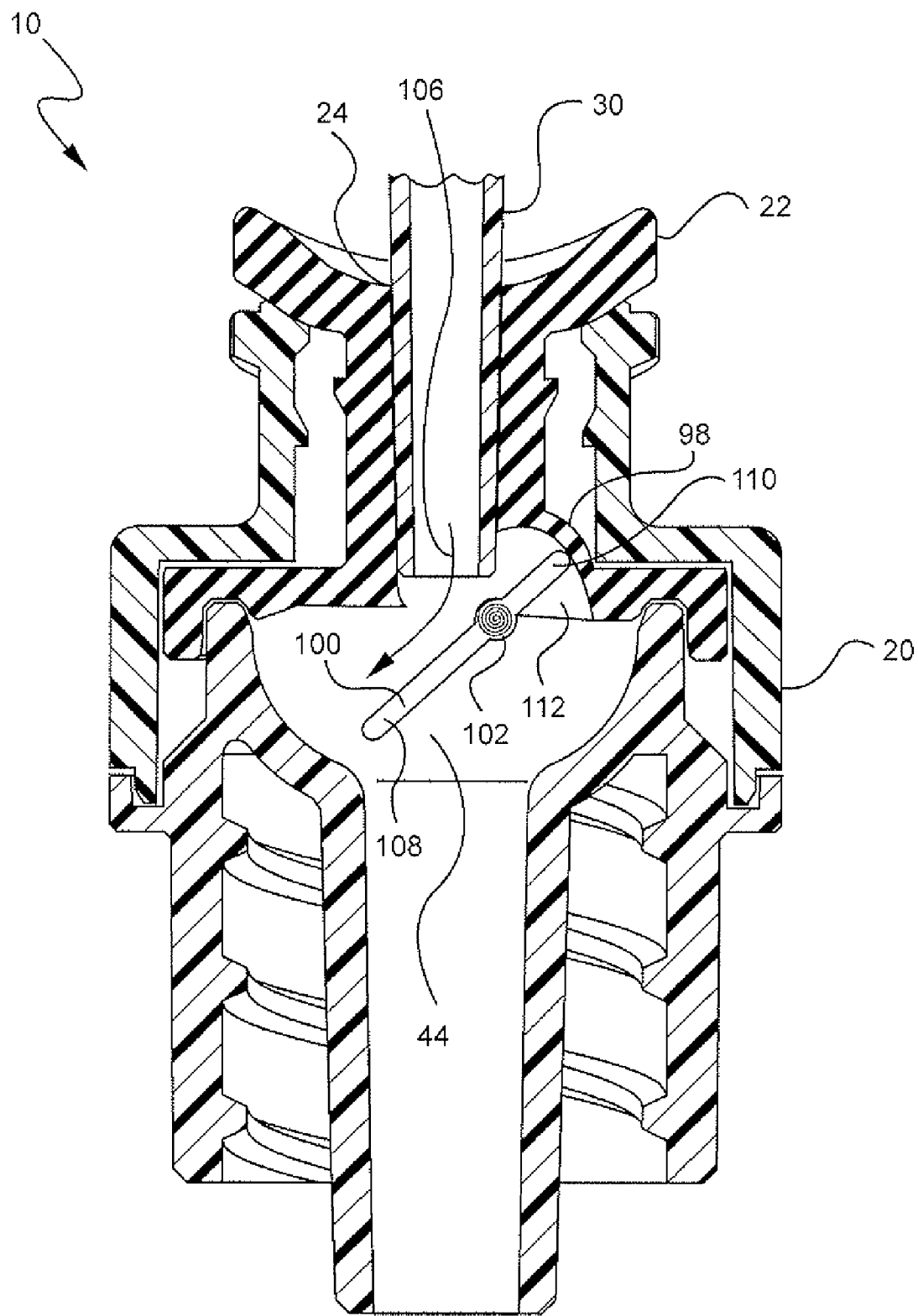
FIG. 16 is a partial cross section view of the vascular access device of FIG. 15 with the spring loaded valve open.

Referring now to FIG. 16, the vascular access device 10 of FIG. 15 is shown with the tip 30 of a separate device 26 inserted into the septum 98. The tip 30 is shown discharging a fluid 106 towards the pivoting member 100. The force of the fluid 106 and/or the force of the mechanical insertion of the tip 30 against a lower wing 108 of the pivoting member 100 causes the pivoting member 100 to rotate in a counter clockwise direction against the tension of the torsion spring 102. When the pivoting member 100 rotates counter clockwise, the lower wing 108 extends into the interior chamber 44 and the upper wing 110 of the pivoting member 100 retracts into a cavity within the wall of the septum 98 to create an increased volume 112. After the fluid 106 has been fully discharged into the interior chamber 44 and the rate of flow has decreased and/or after the tip 30 is removed, the tension of the torsion spring 102 will cause the pivoting member 100 to rotate again clockwise to a position that seals the septum 98 as shown in FIG. 15. Once sealed, the pivoting member 100 prevents any backflow of fluid 106 into the septum chamber where the tip 30 is inserted.

Figure 17:
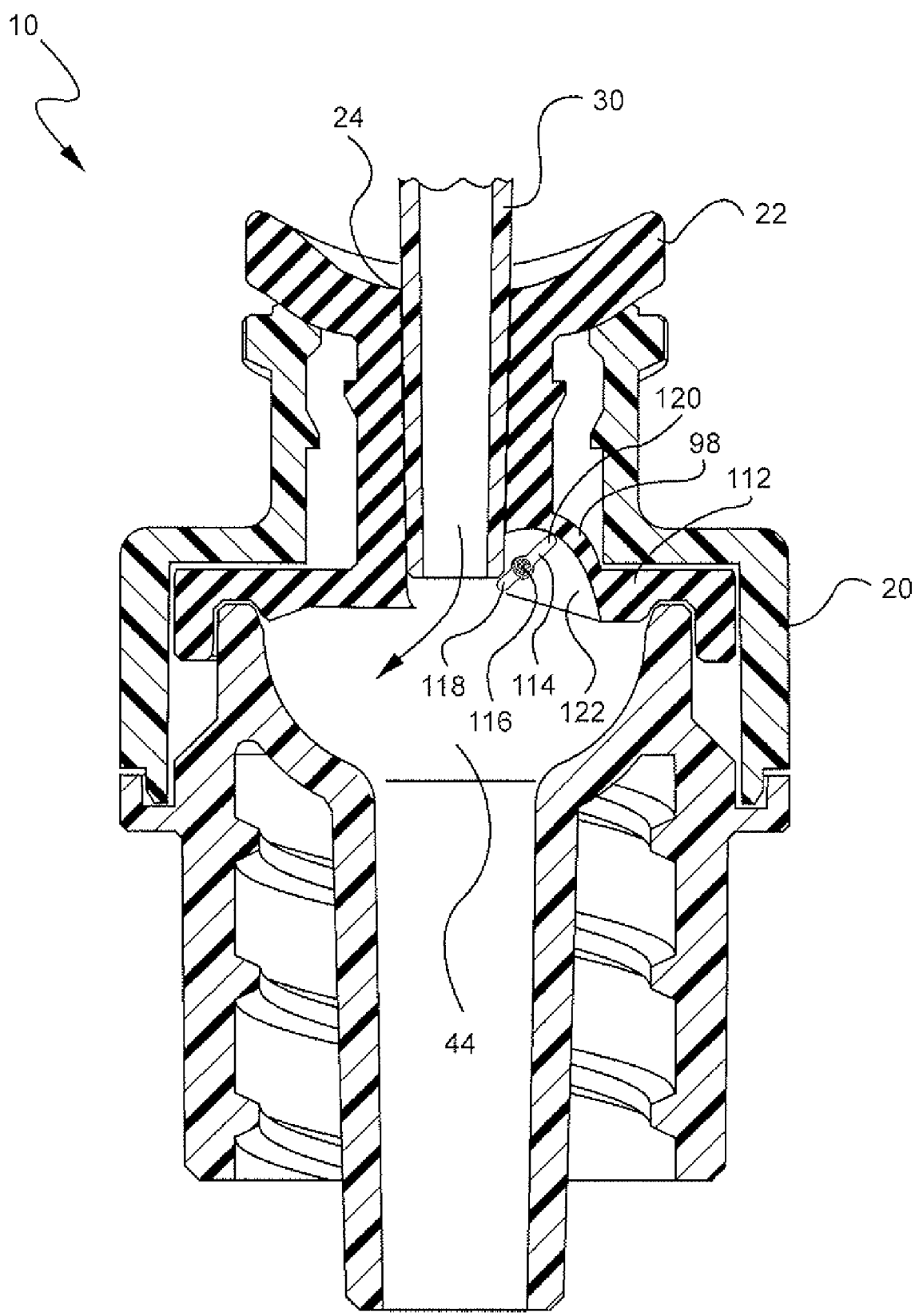
FIG. 17 is a partial cross section view of a vascular access device with a spring loaded valve.

Referring now to FIG. 17, a vascular access device 10 includes a septum 112 and a pivoting member 114 placed under tension of a torsion spring 116. When fluid is infused and/or the tip 30 of a separate device 26 is inserted into the septum 112, the pivoting member 114 rotates counter clockwise against the clockwise tension of the torsion spring 116. When the pivoting member 114 rotates counter clockwise, a lower wing 118 moves into an interior chamber 44 to decrease the volume of the interior chamber 44. Simultaneously, an upper wing 120 is retracted from the interior chamber 44 into a recess of the septum 112 to create a larger volume 122 within the interior chamber 44.

Thus, the vascular access device 10 of FIG. 17 is an alternate embodiment to the vascular access device of FIGS. 15 and 16 which creates more volume than the volume that is used or depleted when the tip 30 accesses the device 10. The increased volume 122 is possible because the upper wing 120 is longer than the lower wing 118, and when the pivoting member 114 rotates counter clockwise a greater amount of volume is created than the amount of volume that is depleted.

The embodiments shown in FIGS. 15 through 17 thus reveal a pivoting member that creates a larger volume within an interior chamber 44 when the pivoting member is activated by the insertion of the tip 30 of a separate, external device 26. Preferably, the length of the various wings and the tension placed on the torsion spring of the pivoting member of the embodiments of FIG. 15 through 17, may be adjusted to ultimately produce a mechanically activated valve that avoids any reflux or displacement of fluid. In this manner, the tip 30 of a separate device 26 may be inserted into the vascular access device 10, fluid may be discharged, and a patient may be treated without the operation of the extravascular system ever resulting in fluid traveling upstream, i.e., from a patient's vascular system to a catheter of the extravascular system.

Figure 18:
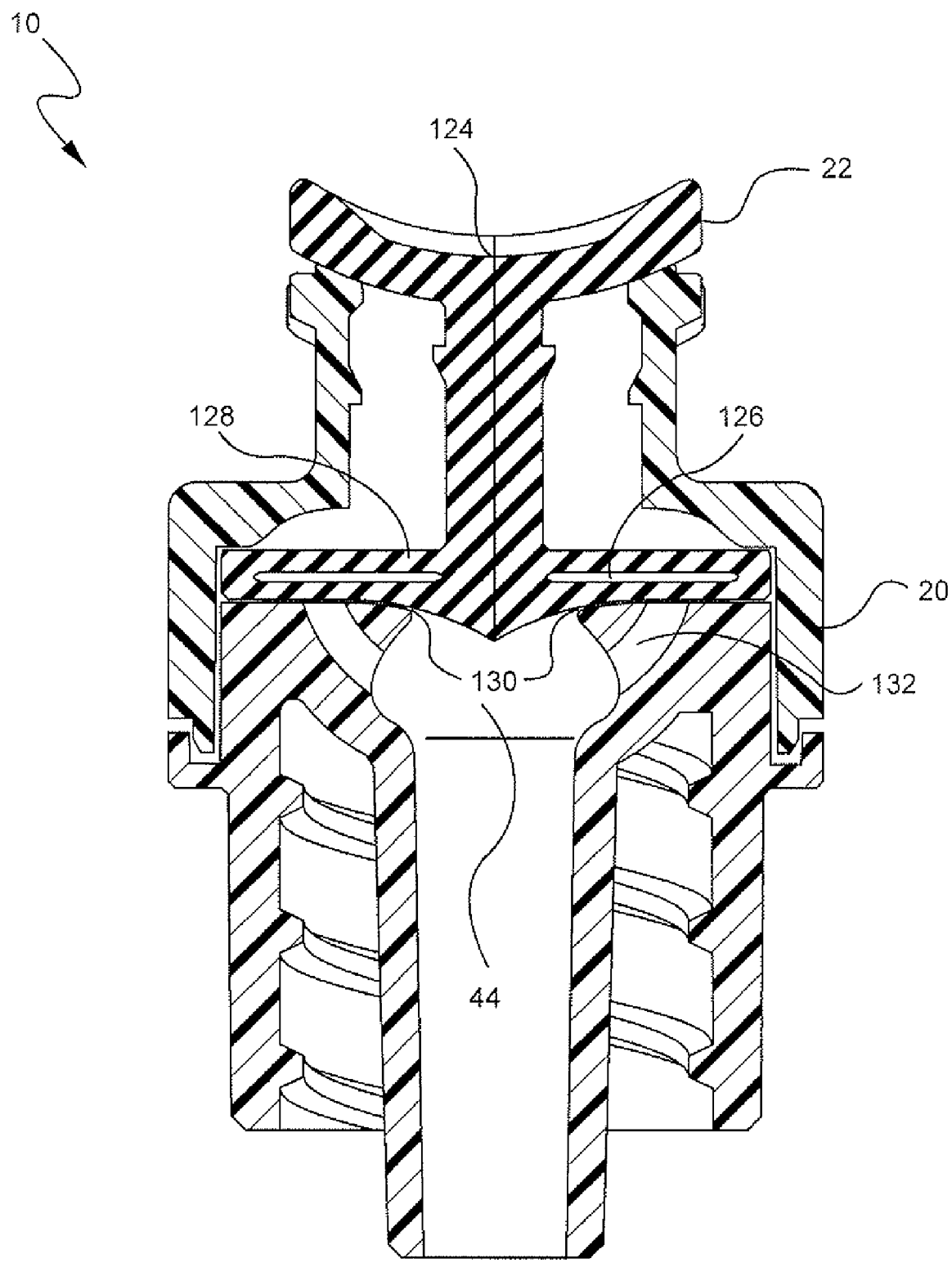
FIG. 18 is a partial cross section view of a vascular access device having a rigid member.

Referring now to FIG. 18, a vascular access device 10 includes an elastomeric septum 124 with a rigid spring and pivoting member 126 embedded in the base 128 of the septum 124. The base 128 of the septum 124 rests upon a fulcrum or pivot point 130. The device 10 also includes a channel 132 located between the pivot point and the body 20 of the device 10.

Figure 19:
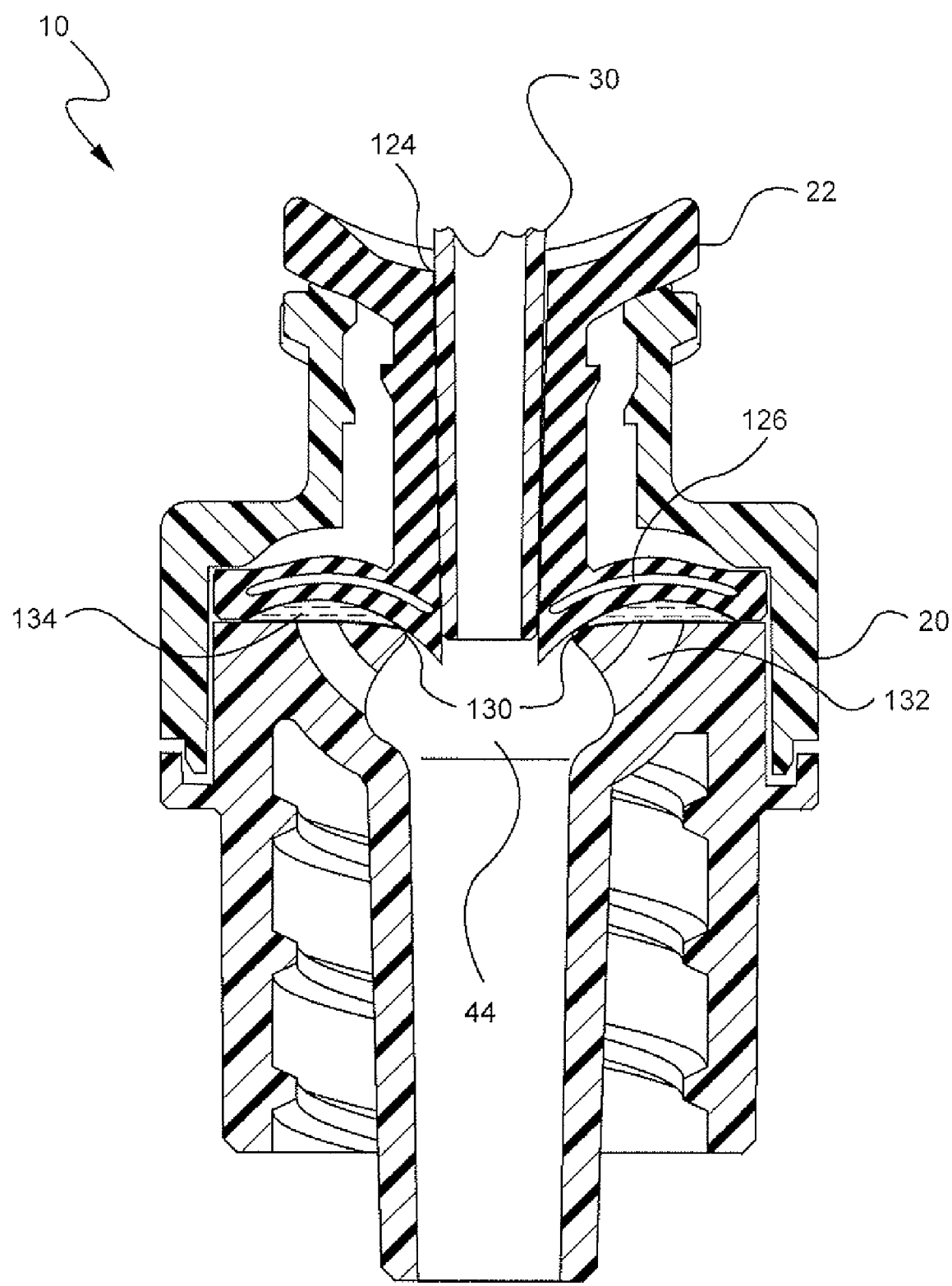
FIG. 19 is a partial cross section view of the vascular access device of FIG. 18 with the tip of a separate device inserted.

Referring now to FIG. 19, the vascular access device 10 of FIG. 18 is shown with the tip 30 of a separate device 26 inserted into the septum 124. With the tip 30 fully inserted into the septum 124, the rigid spring member 126 is forced to bend or otherwise buckle in order to create a cavity 134 in which fluid is stored. The fluid enters the created cavity 134 through the flow channel 132 as the rigid spring member 126 is bent in an upward arched shape. As the tip 30 is removed from the septum 124, the pressure placed on the spring member 126 is removed causing the spring member 126 to return to its original position as shown in FIG. 18. When the spring member 126 returns to its original position, the cavity 134 disappears as the fluid that was once stored within the cavity 134 travels through the flow channel 132 and into the interior chamber 44.

Thus, the embodiment described with reference to FIGS. 18 and 19 includes a spring member which gradually increases the overall volume of the interior chamber 44 as a tip 30 of a separate device 26 is inserted into the septum 124 of a vascular access device 10. The spring member 126 may, in other embodiments, take any form, shape, or size. For example, in one embodiment, the spring member may be a bistable spring as mentioned earlier. When actuated by a Luer or other tip 30 of an external or separate device 26, a bistable spring member will rapidly change shape, or otherwise buckle, in order to create or increase the overall volume of the interior chamber 44. Subsequently, when the tip 30 of a device 10 is removed, the bistable spring will rapidly resume its posture to its original position, causing the chamber beneath it to collapse and the overall volume of the interior chamber 44 to decrease.

Figure 20:
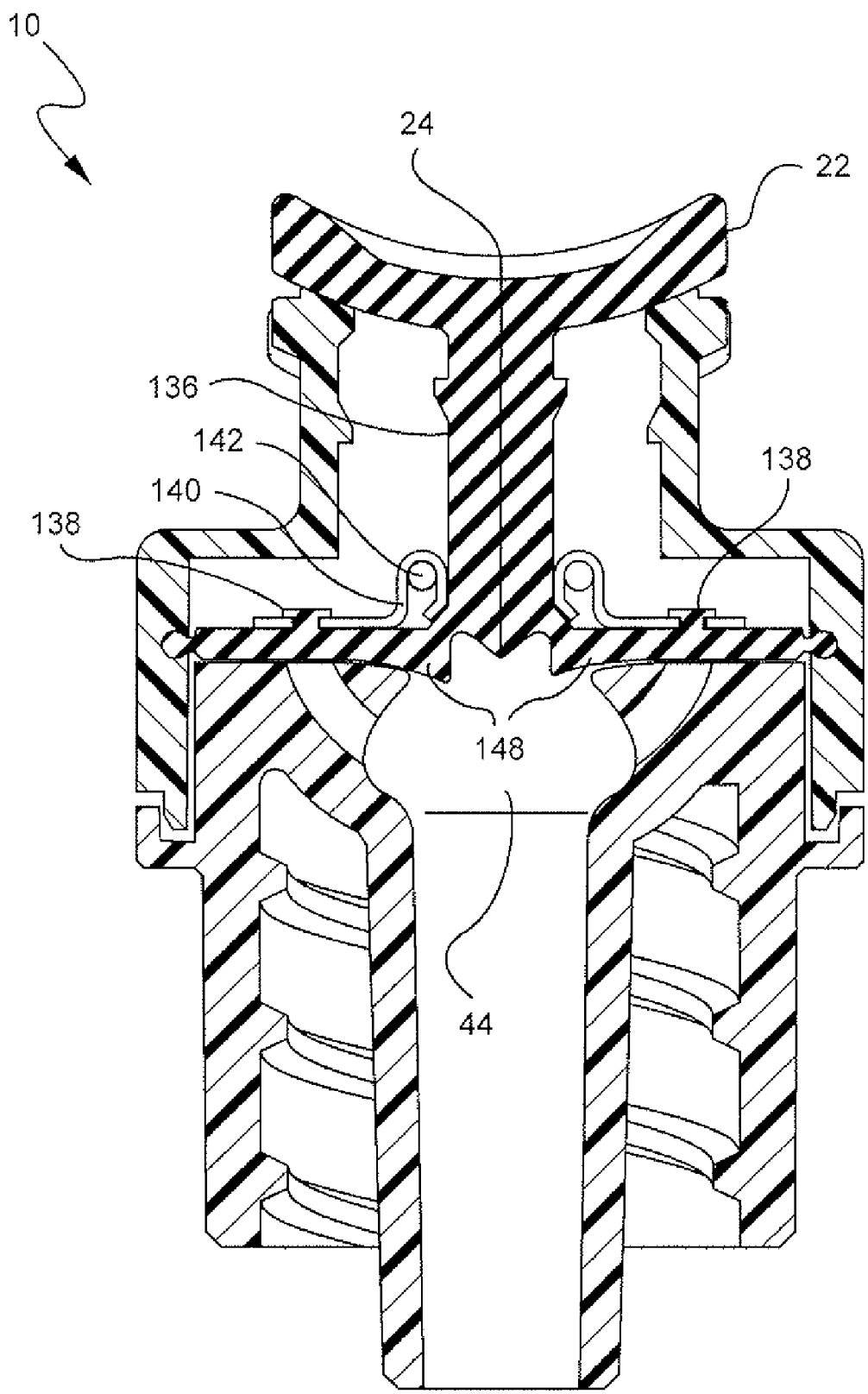
FIG. 20 is a partial cross section view of a vascular access device and a rotational clip.
Figure 20A:
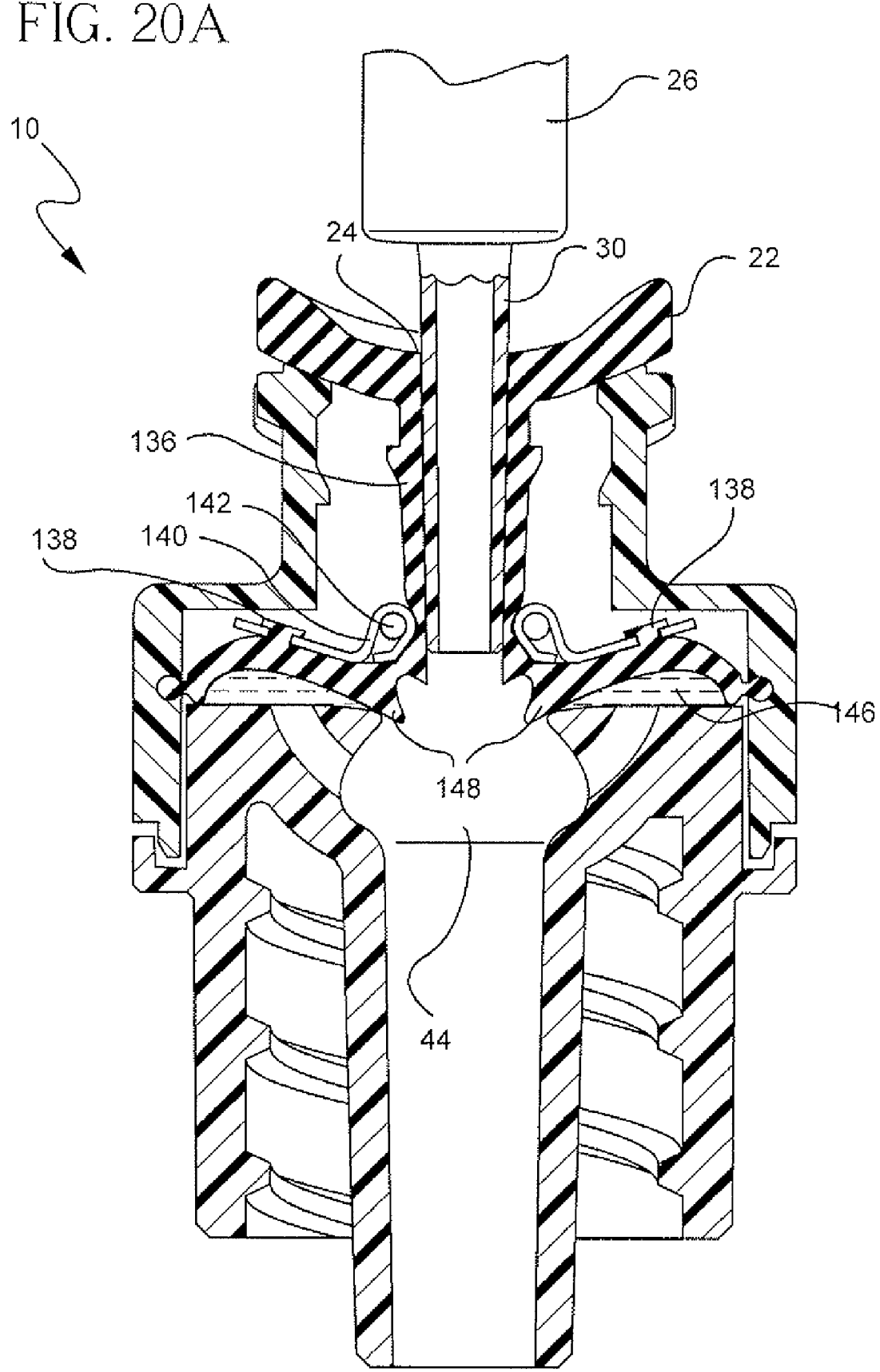
FIG. 20A is a partial cross section view of the vascular access device illustrated in FIG. 20 with a separate device inserted.

Referring now to FIG. 20, a septum 136 of a vascular access device 10 includes a knob 138 attached to a metal clip 140 that rotates or otherwise pivots upon a pin 142. FIG. 20 shows a vascular access device 10 that is not yet engaged or is disengaged with a separate device 26. FIG. 20A shows the vascular access device 10 as engaged with a separate device 26. In FIG. 20A the tip 30 of the separate device 26 is fully inserted into the septum 136 causing the metal clip 140 to rotate in a counter clockwise direction 144 around the pin 142. The counter clockwise rotation of the metal clip 140 causes the metal clip 140 to raise the knob 138, thus creating an increased volume 146 within an interior chamber 44. When the separate device 26 is later removed, the metal clip 140 which is placed on a pre-loaded spring, restores the base, or diaphragm, 148 of the septum 136 to its original position. When the base 148 is returned to its original position, the internal fluid volume of the interior chamber 44 is decreased, causing fluid to flow from the extravascular system (to which the device 10 and separate device 26 are attached) to the vascular system of a patient.

Figure 21:
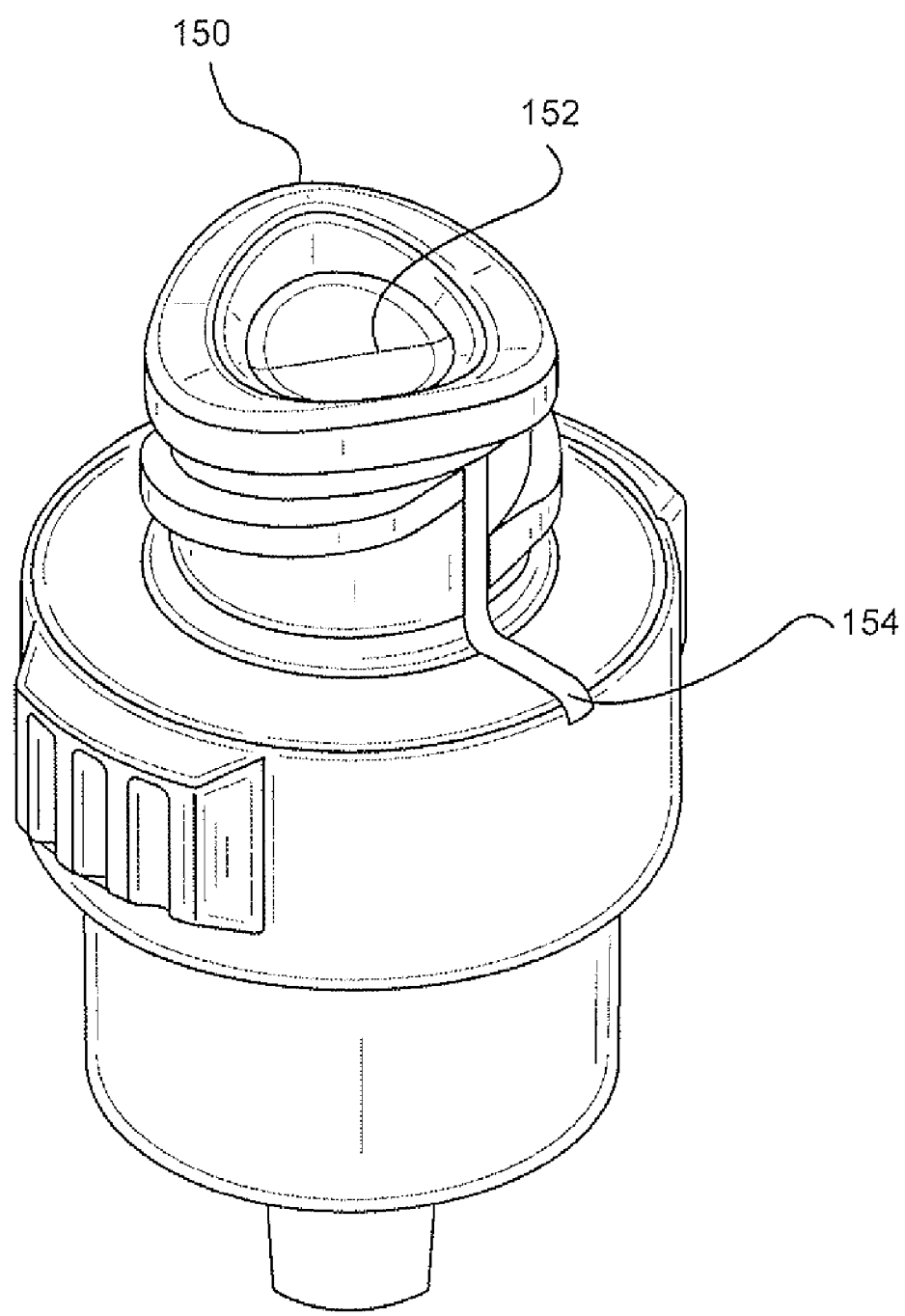
FIG. 21 is a perspective view of a vascular access device.
Figure 22:
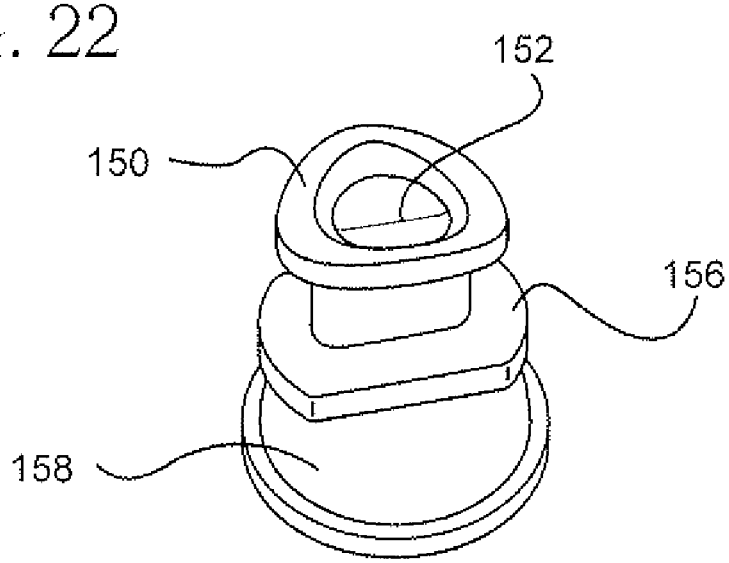
FIG. 22 is a perspective view of a vascular access device including the septum with a reservoir.
Figure 23:
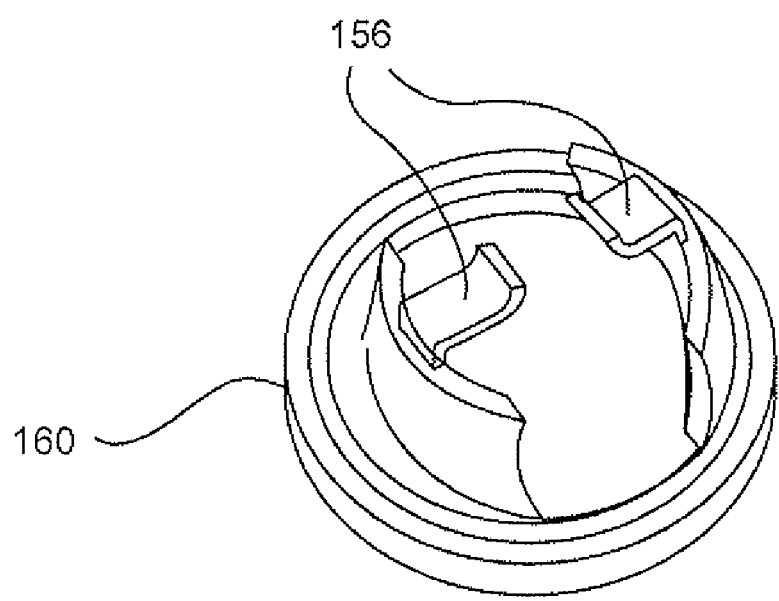
FIG. 23 is a perspective view of an annular member with spring fingers.

Referring now collectively to FIGS. 21 through 23, a vascular access device 10 includes a septum 150 with a slit 152 and at least one clearance slot 154 through which at least one spring finger 156 may articulate. The septum 150 includes a reservoir 158 at its base. An annular structure 160 may include at least one spring finger 156. The annular structure 160 includes a lumen through which the septum 150 may be placed.

Figure 24:
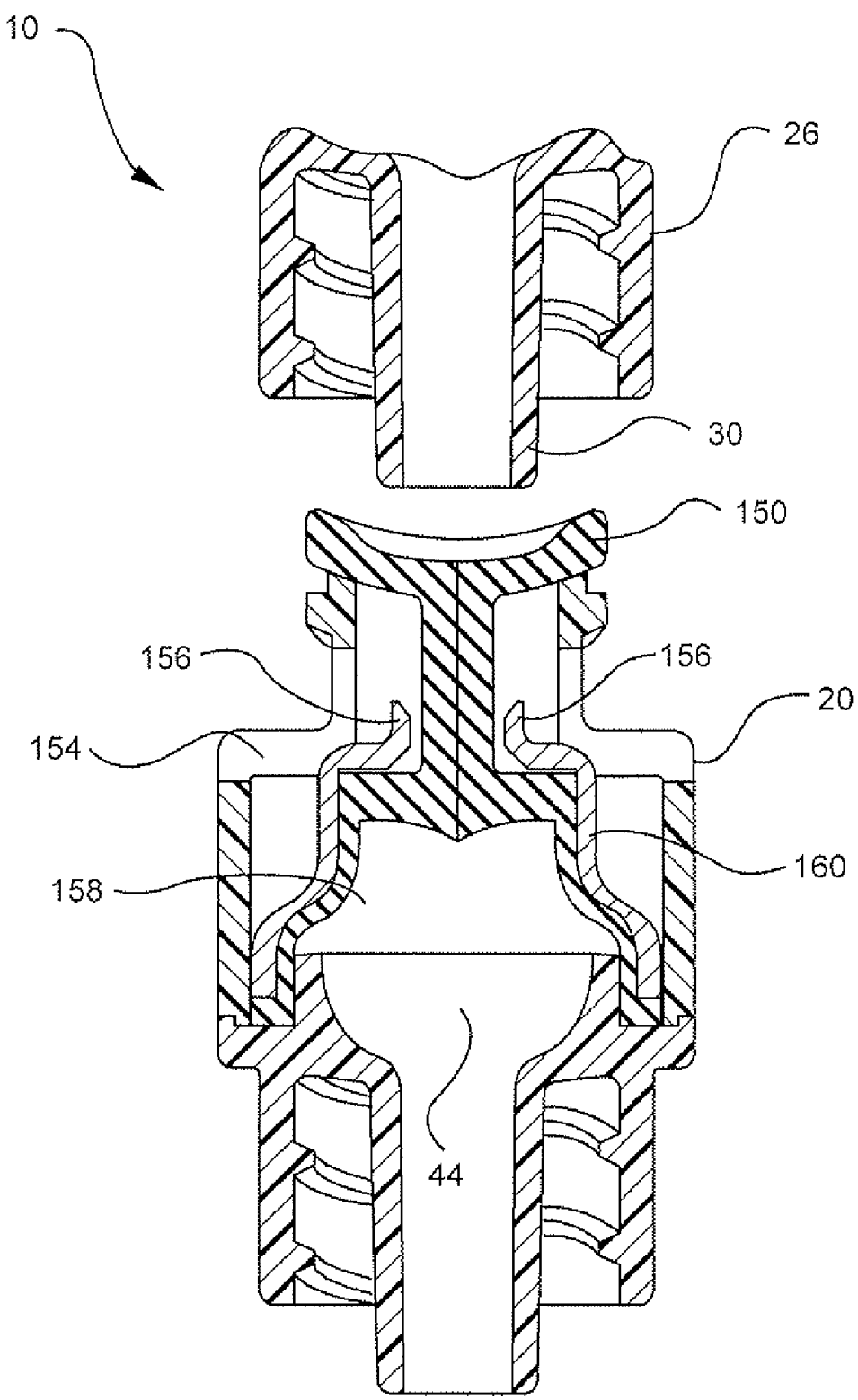
FIG. 24 is a cross section view of a vascular access device with a collapsed reservoir.

Referring now to FIG. 24, a cross-section of the vascular access device 10 of FIG. 21 is shown engaged with the septum 150 of FIG. 22 and the annular member 160 of FIG. 23. The combination of the body 20 of the vascular access device 10, the septum 150, and the annular member 160 is shown in resting position, prior to access by the tip 30 of a separate device 26. In its resting state, the spring fingers 156 of the annular member 160 force the septum 150 closed, which in turn causes the reservoir 158 to be compressed. When the reservoir 158 is compressed, an interior chamber 44 has a relatively smaller internal volume.

Figure 25:
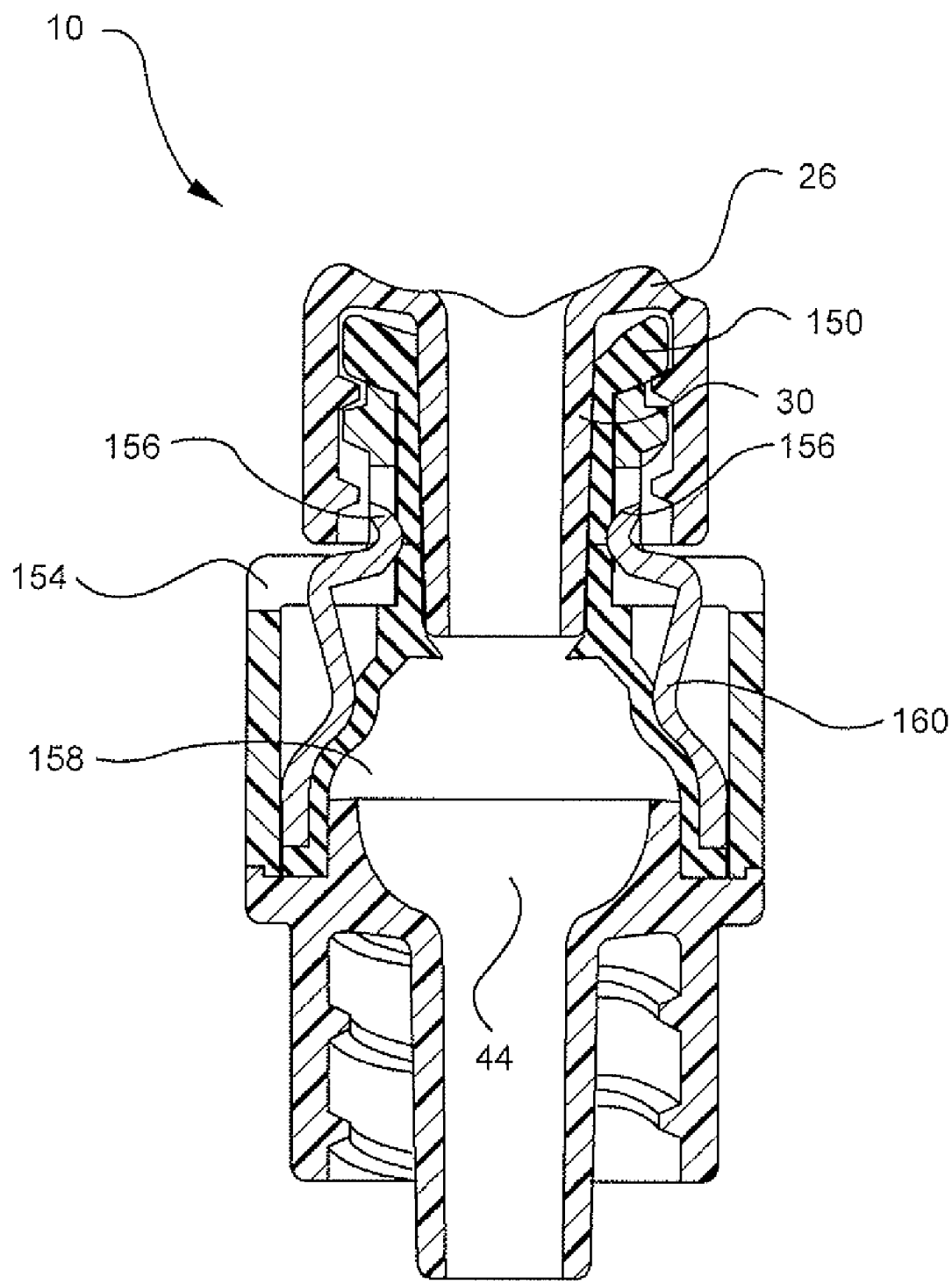
FIG. 25 is a cross section view of the vascular access device of FIG. 24 showing the reservoir full.

Referring now to FIG. 25, the vascular access device 10 of FIG. 24 is shown fully engaged with the separate device 26 such that the tip 30 is fully inserted into the septum 150. Upon full insertion, the tip 30 causes the spring fingers 156 to separate outwards through the clearance slots 154 which are shown in FIG. 21. With the spring fingers 156 extending outwards through the clearance slots 154, the base or bottom of the septum 150 has more room to expand just above the reservoir 158. When the base of the septum 150 expands just above the reservoir 158, the reservoir also expands causing an increased amount of volume within the interior chamber 44. Subsequently, when the tip 30 is removed from the device 10, the spring fingers 156 will move inwardly from the clearance slots 154 towards the septum 150, causing the septum 150 to close the body of the septum 150 to compress upon the reservoir 158 and the reservoir to collapse to its original starting position as shown in FIG. 24. This action of moving the reservoir 158 from a decompressed to a compressed state will cause the internal volume of the interior chamber 44 to decrease, which in turn causes fluid to flow from the interior chamber 44 through the extravascular system and into the vascular system of a patient. This flow of fluid will prevent any unwanted reflux of blood or other fluid from a patient's vascular system into the extravascular system.

Figure 26:
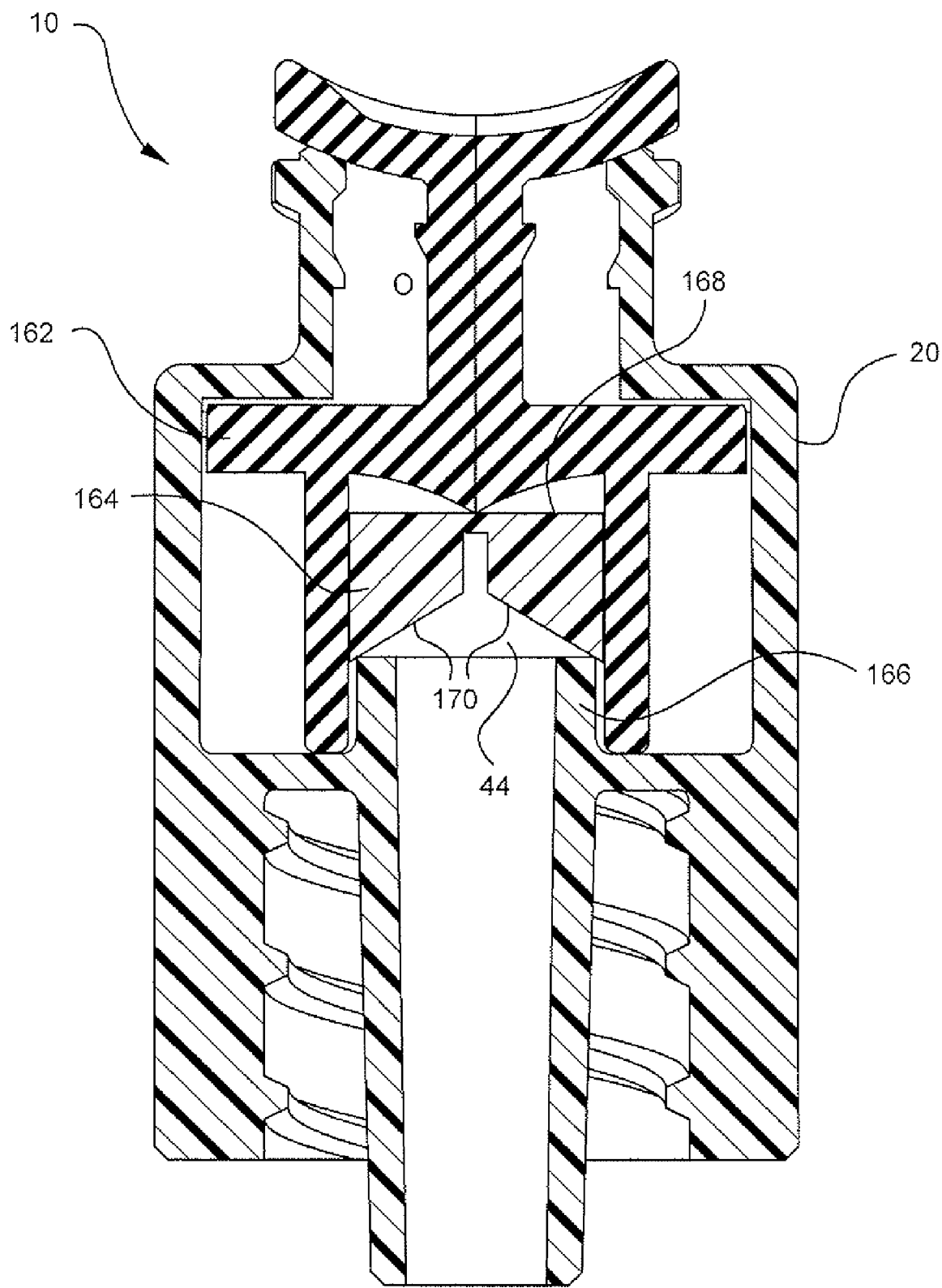
FIG. 26 is a partial cross section view of a vascular access device with a split wedge.
Figure 27:
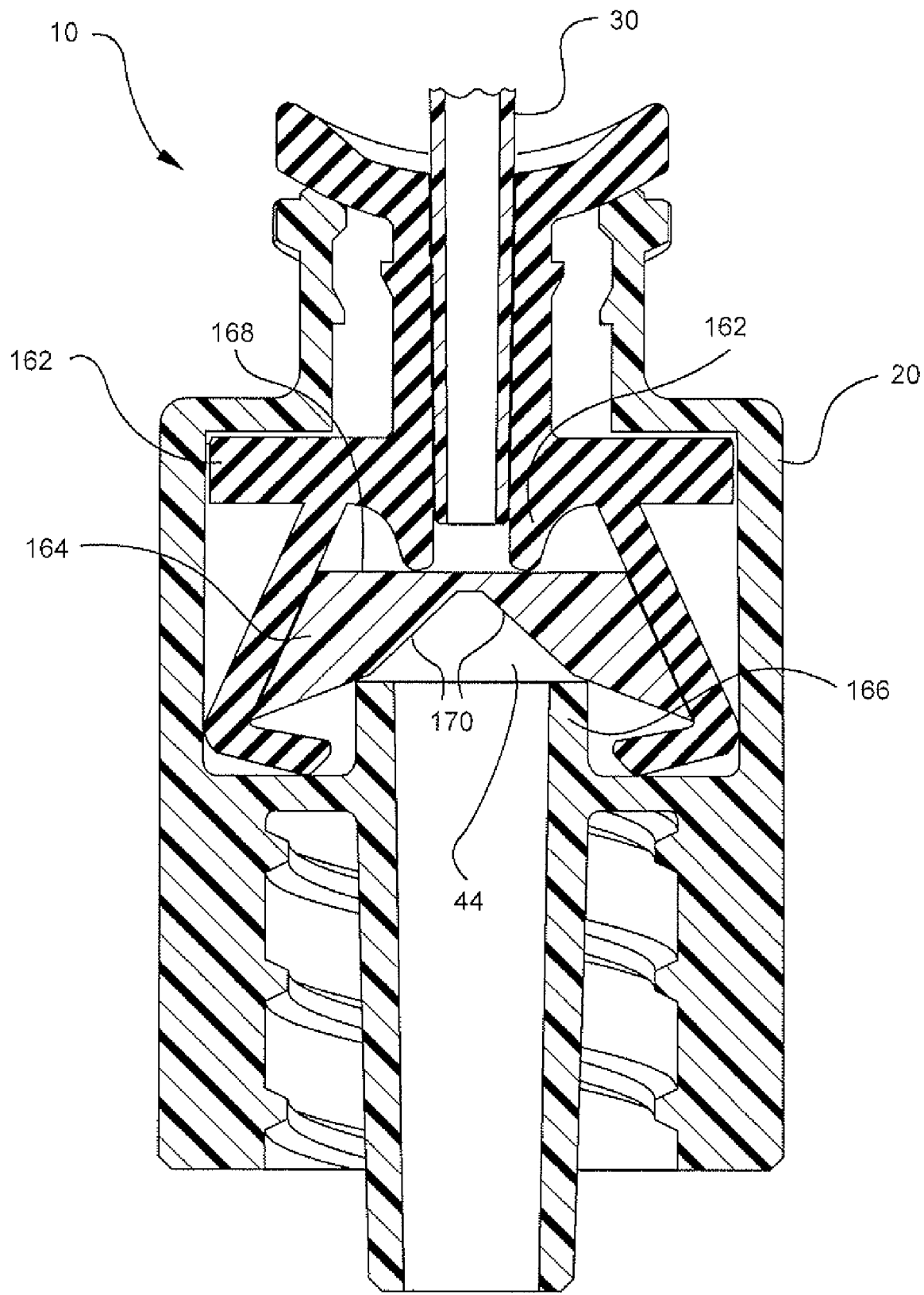
FIG. 27 is a partial cross section view of the vascular access device of FIG. 26 with the split wedge in open position.

Referring now to FIG. 26, a vascular access device 10 includes a body 20 and an elastomeric slit septum 162. A split wedge 164 resides within a lower chamber 44 of the septum 162. The split wedge is capable of separating its bottom angled surface when coerced by the tip 30 of a separate device 26 against a rigid base member 166 that resides beneath the split wedge 164. Referring now to FIG. 27, the vascular access device 10 of FIG. 26 is shown with the tip 30 of a separate device 26 fully engaged within the septum 162. When the tip 30 places force upon the top surface 168 of the split wedge 164, the bottom angled surfaces 170 of the split wedge 164 are pressed against the surface of the rigid structure 166, causing the split wedge 164 to separate. When the split wedge 164 separates, the elastic walls of the septum 162 also separate causing the internal volume of the interior chamber 44 to increase. The internal volume of the interior chamber 44 increases both between the legs of the split wedge 164 and on the sides of the rigid structure 166.

Figure 28:
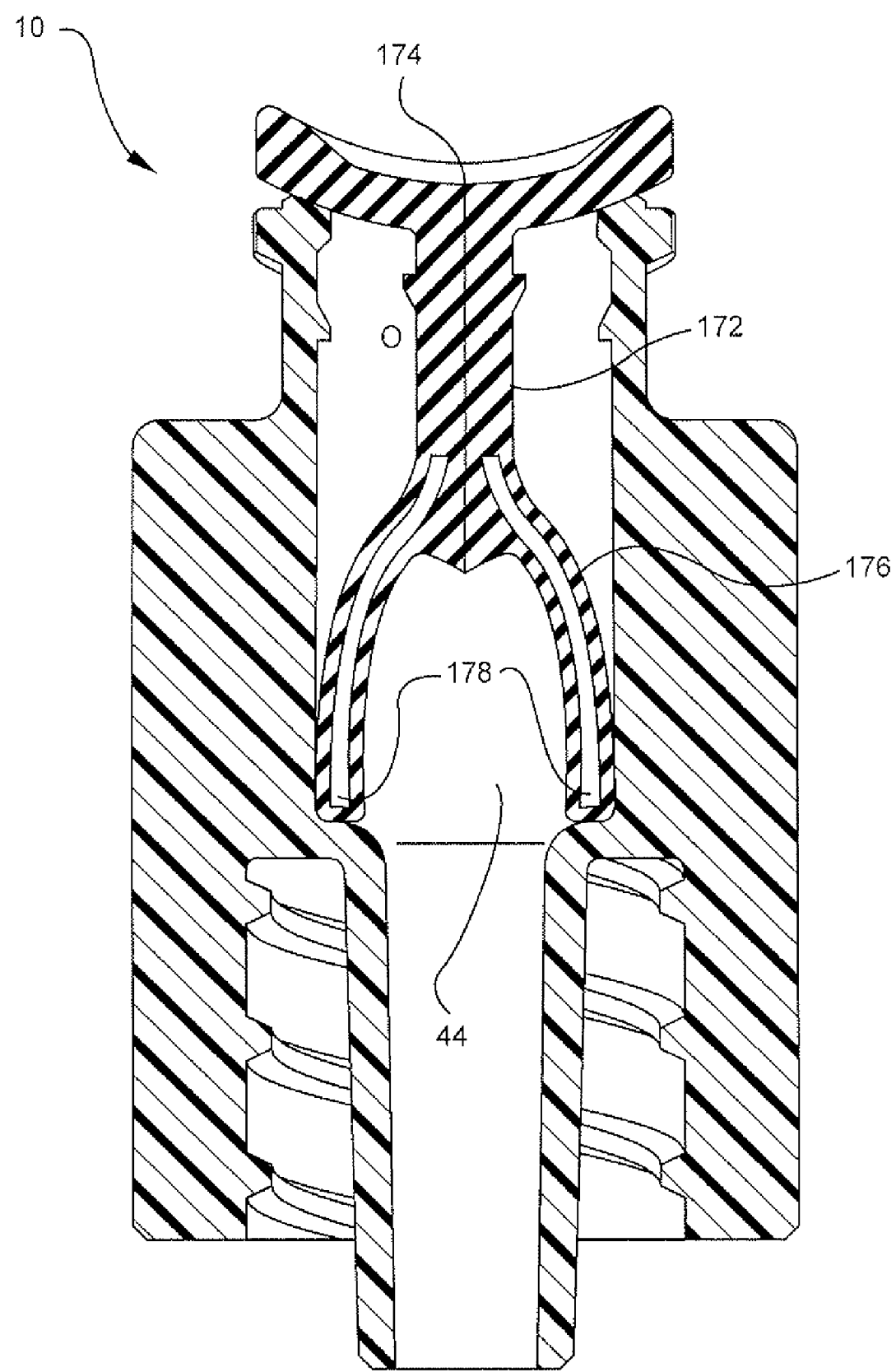
FIG. 28 is a partial cross section view of a vascular access device with two curved pivoting members.

Referring now to FIG. 28, a vascular access device 10 includes a septum 172 with a slit 174 and at least one curved, rigid, pivoting member 176. The pivoting members 176 are fixed to a pivot point 178 against the body 20 of the vascular access device 10.

Figure 29:
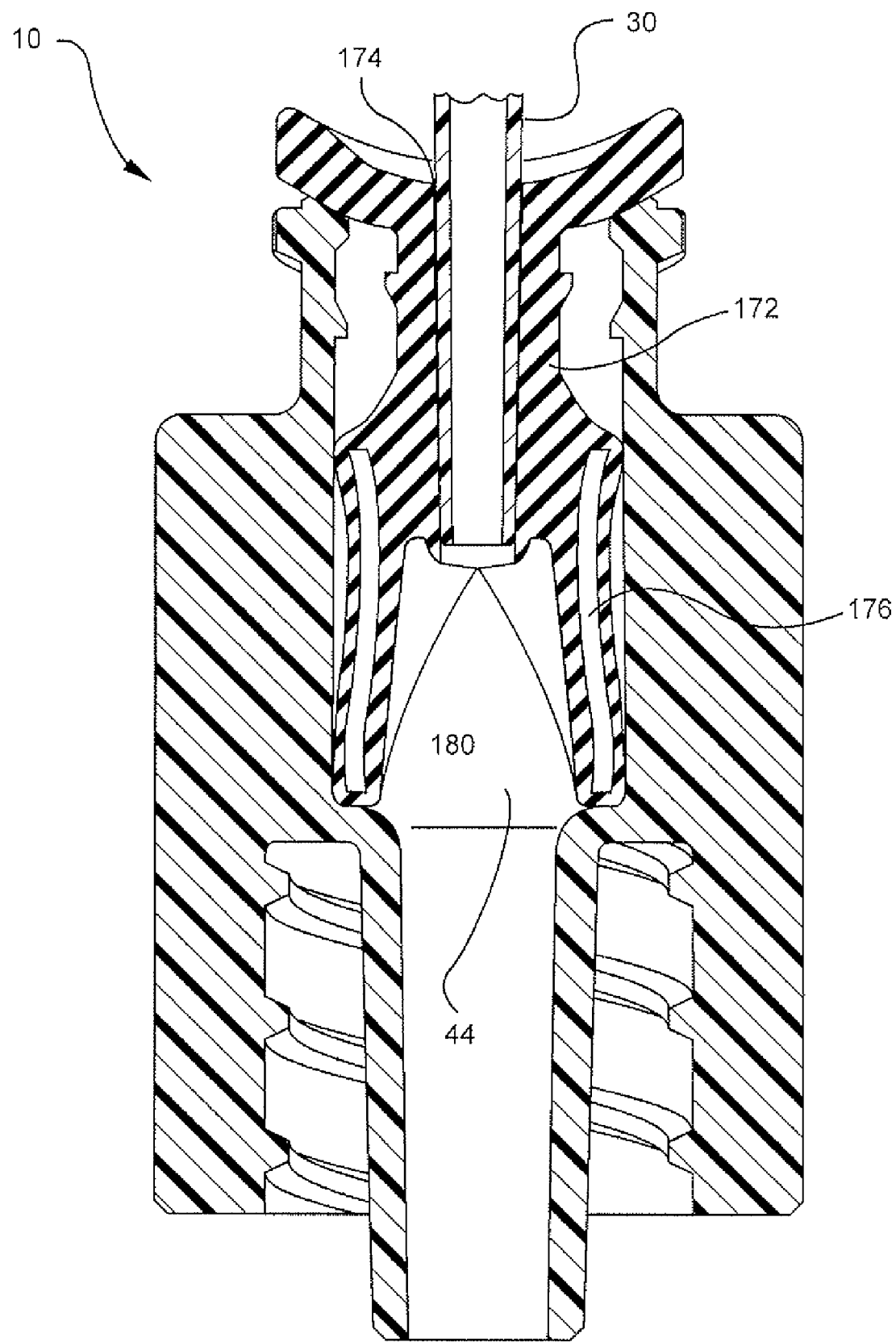
FIG. 29 is a partial cross section view of the vascular access device of FIG. 28 the tip of a separate device inserted.

Referring now to FIG. 29, the vascular access device 10 of FIG. 28 is shown with the tip 30 of a separate device 26 fully engaged with the septum 172. When the tip 30 is fully inserted into the slit 174, the pivoting members 176 that are embedded within the septum 172 are forced outward against the walls of the body 20 of the device 10. In their outward position, the pivoting curved members 176 open to increase the amount of internal volume within the interior chamber 44 beneath the closure of the septum 172. The space 180 that is created during tip 30 insertion is later eliminated when the tip 30 is removed from the device 10. As this volume is eliminated, the fluid residing therein is forced from the extravascular system toward the vascular system of a patient.

Figure 30:
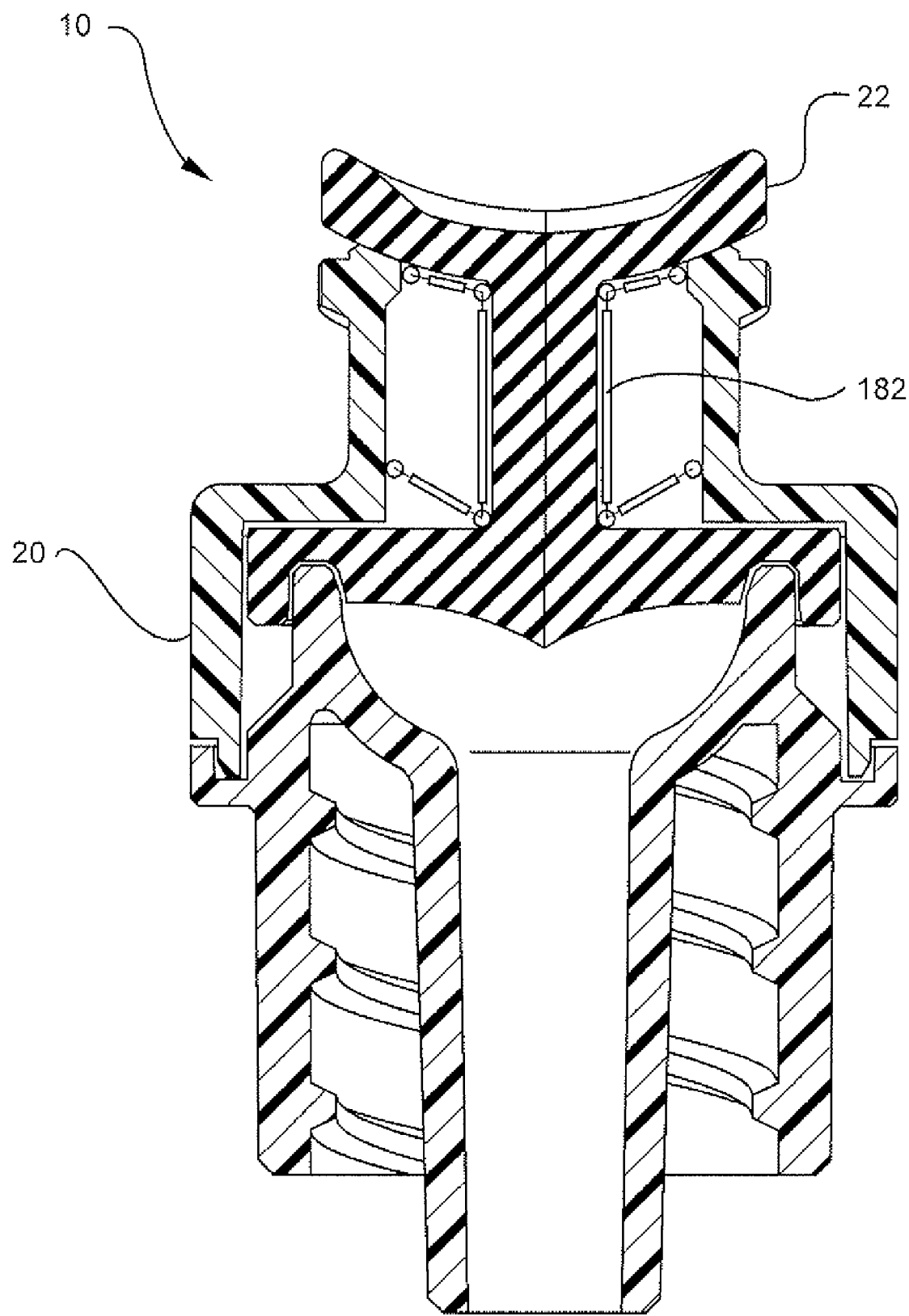
FIG. 30 is a partial cross section view of a vascular access device with a four-bar mechanism.

Referring now to FIG. 30, the vascular access device 10 includes a septum 22 and a four-bar mechanism 182 that is separate and resides on an exterior surface of and in communication with the septum 22. The four-bar mechanism 182 is anchored to the outer wall of the body 20 of the device 10.

Figure 31:
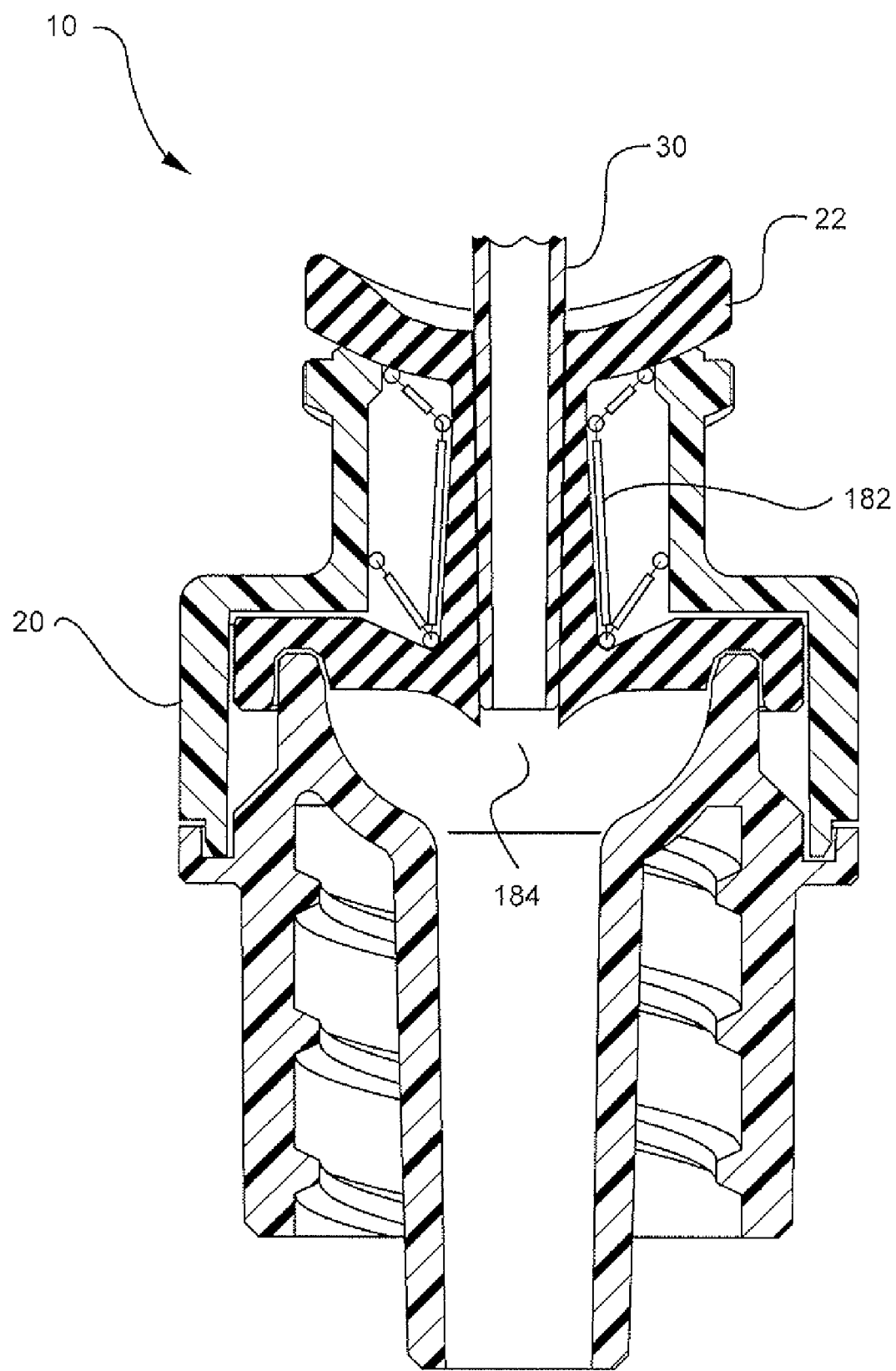
FIG. 31 is a partial cross section view of the vascular access device of FIG. 30 with the tip of a separate device inserted.

Referring now to FIG. 31, the vascular access device 10 of FIG. 30 is shown with the tip 30 of a separate device 26 inserted into the septum 22. With normal slit septums that do not include a four-bar mechanism as that shown in FIGS. 30 and 31, when a tip 30 is inserted into a slit septum, only that portion of the septum that is in direct contact with the tip is biased open with a minimal amount of material of the septum 22 in front of the end of the tip 30. However, the four-bar mechanism 182 of FIG. 31 permits the septum 22 to open along its entire length when the tip 30 is initially inserted into the top portion of the septum 22. As the four-bar mechanism 182 opens the entire length of the septum 22, a volume 184 is created within the septum 22 as the tip 30 is initially advanced. The increased volume 184 is added to the volume beneath it in the extravascular system, and when the tip 30 is removed from the device 10, the four-bar mechanism 182 collapses causing the volume 184 to be eliminated. When the volume 184 is eliminated, fluid is expelled from that volume through the extravascular system and into the vascular system of a patient.

Figure 32:
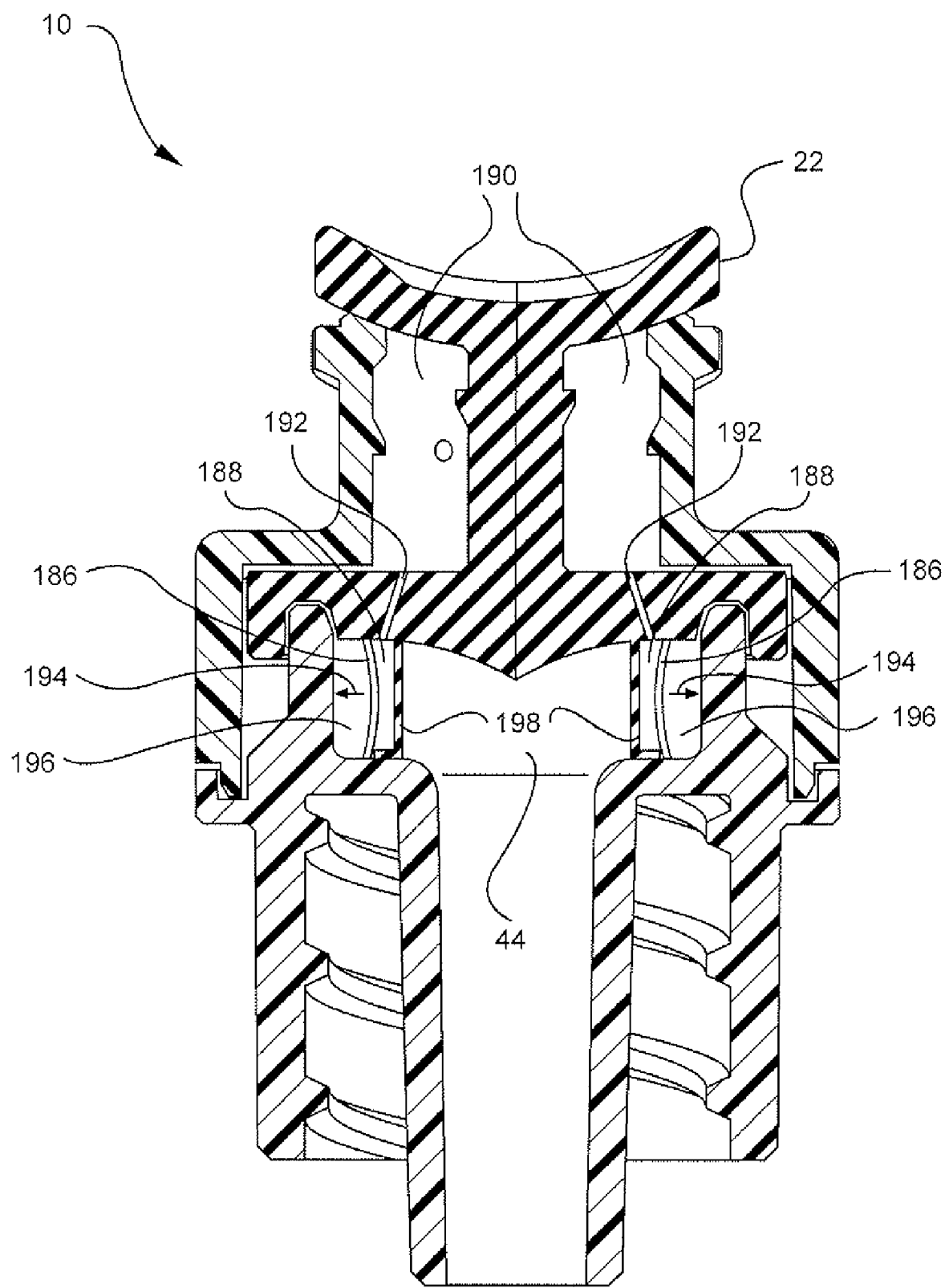
FIG. 32 is a cross section view of a vascular access device with a rigid member.

Referring now to FIG. 32, a vascular access device 10 includes a septum 22 and a rigid member 186 capable of being displaced by an air pressure chamber 188 that may be disturbed when the tip 30 of a separate device 26 is inserted into the septum 22. The rigid member 186 may be a bistable spring capable of flexing in alternating directions under the influence of opposing force exerted upon the body of the spring.

As the tip 30 is inserted into the septum 22, an upper chamber 190 decreases in size, forcing air through a channel 192 in the septum 22, to an air pressure chamber 188 neighboring the rigid member 186. As the pressure within a neighboring chamber 188 increases, the bistable spring of the rigid member 186 will flex in a direction 194 into an expansion chamber 196. As the rigid member 186 flexes in a direction 194, the vacuum existing in the neighboring chamber 188 will pull an internal wall 198 in the direction 194, causing the volume of an interior chamber 44 to increase.

As the tip 30 is retracted from the septum 22, the upper chamber 190 will increase in size, pulling air from air pressure chamber 188 through the channel 192 into the upper chamber 190. As the pressure within the air pressure chamber 188 decreases, the bistable spring of the rigid member 186 will flex in a direction opposite direction 194 to return to its original position, causing the internal wall 198 to also return to its original position, and causing the volume of the interior chamber 44 to decrease to its original volume prior to tip 30 insertion. The stress placed upon the bistable spring is such that only minimal force or pressure is required to engage the bistable spring in either direction.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
   a vascular access device including a body having an access port, wherein an inner surface of the body forms a fulcrum, and wherein the access port forms a fluid flow path through the vascular access device;

a septum positioned within the access port, the septum having a slit through which a separate extravascular device may be inserted into the access port of the vascular access device; and a rigid, T-shaped pivoting member embedded within a wall of the septum and outside the fluid flow path, wherein the pivoting member pivots against the fulcrum when the port is accessed by the separate extravascular device such that upon removal of the separate extravascular device fluid is not drawn into the medical device.

2. The medical device of claim 1, wherein the body of the vascular access device further includes an interior chamber and an outer chamber, wherein the interior chamber is inside the fluid flow path, and wherein the outer chamber is outside the fluid flow path.

3. The medical device of claim 2, wherein the rigid, T-shaped pivoting member pivots as the separate extravascular device is inserted into the access port causing the portion of the septum within which the rigid pivoting member is embedded to move into the outer chamber to thereby increase the volume of the interior chamber.

4. The medical device of claim 3, wherein the body of the vascular access device further includes one or more channels adapted to allow air to escape the outer chamber as the septum moves into the outer chamber.

5. The medical device of claim 2, wherein the rigid pivoting member is embedded within a silastic material that extends from the septum.

6. The medical device of claim 5, wherein the septum and the silastic material that extends from the septum are integrally formed.

7. The medical device of claim 5, wherein the septum and the silastic material extending from the septum are formed separately and bonded together.

8. The medical device of claim 5, wherein the silastic material extending from the septum is formed to include at least one fold along its cross section when the silastic material is in a first resting position.

9. The medical device of claim 8, wherein the at least one fold straightens as the separate extravascular device is inserted into the access port to thereby increase the volume in the interior chamber, the silastic material assuming a second opened position.

10. The medical device of claim 9, wherein the at least one fold returns as the separate extravascular device is removed from the access port to thereby decrease the volume in the interior chamber, the silastic material resuming the first resting position.

11. The medical device of claim 10, wherein the decrease in volume within the interior chamber results in zero net volume displacement within the interior chamber as the separate extravascular access device is removed from the access port.

12. The medical device of claim 10, wherein the decrease in volume within the interior chamber results in a volume that is displaced distally from the interior chamber as the separate extravascular access device is removed from the access port.

13. The medical device of claim 10, wherein the slit in the septum is closed under the force of the fold formed in the silastic material extending from the septum as the separate extravascular access device is removed from the access port.

14. The medical device of claim 1, wherein the rigid pivoting member is rigid relative to the materials comprising the septum within which it is embedded.

15. A medical device, comprising:

a vascular access device including a body having an access port, wherein an inner surface of the body forms a fulcrum, and wherein the access port forms a fluid flow path through the vascular access device;

a septum positioned within the access port, the septum having a slit through which a separate extravascular device may be inserted into the access port of the vascular access device; and a rigid pivoting member embedded within a wall of the septum and outside the fluid flow path, wherein the pivoting member pivots against the fulcrum when the port is accessed by the separate extravascular device such that upon removal of the separate extravascular device fluid is not drawn into the medical device.

16. The medical device of claim 15, wherein the body of the vascular access device further includes an interior chamber and an outer chamber, wherein the interior chamber is inside the fluid flow path, and wherein the outer chamber is outside the fluid flow path.

17. The medical device of claim 15, wherein the body of the vascular access device further includes one or more channels adapted to allow air to escape the outer chamber as the septum moves into the outer chamber.

18. The medical device of claim 15, wherein the rigid pivoting member is embedded within a silastic material that extends from the septum.

19. The medical device of claim 15, wherein the silastic material extending from the septum is formed to include at least one fold along its cross section when the silastic material is in a first resting position.

20. The medical device of claim 15, wherein the rigid pivoting member is rigid relative to the materials comprising the septum within which it is embedded.

\* \* \* \* \*